(12) United States Patent
Lyu et al.

(10) Patent No.: US 7,887,932 B2
(45) Date of Patent: Feb. 15, 2011

(54) ORGANOSILOXANE COMPOUND AND ORGANIC LIGHT-EMITTING DEVICE COMPRISING THE SAME

(75) Inventors: Yi-Yeol Lyu, Yongin-si (KR); Jong-Jin Park, Guri-si (KR); Byoung-Ki Choi, Hwaseong-si (KR); Myeong-Suk Kim, Suwon-si (KR); Sung-Hun Lee, Seoul (KR); Lyong-Sun Pu, Suwon-si (KR); Ok-Kyung Cho, Seoul (KR); Young-Mok Son, Hwaseong-si (KR); O-Hyun Kwon, Seoul (KR); Young-Hun Byun, Yongin-si (KR); Das Rupasree Ragini, Suwon-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 1186 days.

(21) Appl. No.: 11/448,142

(22) Filed: Jun. 7, 2006

(65) Prior Publication Data

US 2007/0048532 A1   Mar. 1, 2007

(30) Foreign Application Priority Data

Aug. 26, 2005   (KR) .................. 10-2005-0078720

(51) Int. Cl.
*H01L 51/54* (2006.01)
*C09K 11/06* (2006.01)
*C07F 7/18* (2006.01)

(52) U.S. Cl. .............. 428/690; 428/917; 556/450; 556/453; 313/504; 548/219; 548/440; 544/38

(58) Field of Classification Search ............... 428/690
See application file for complete search history.

(56) References Cited

U.S. PATENT DOCUMENTS

| | | | |
|---|---|---|---|
| 4,356,429 A | 10/1982 | Tang | |
| 4,672,265 A | 6/1987 | Eguchi et al. | |
| 5,645,948 A * | 7/1997 | Shi et al. | 428/690 |
| 5,728,801 A | 3/1998 | Wu et al. | |
| 5,821,309 A | 10/1998 | Oka | 525/540 |
| 5,834,100 A | 11/1998 | Mark et al. | 428/209 |
| 6,201,051 B1 | 3/2001 | Mager et al. | |
| 6,214,937 B1 | 4/2001 | Kennedy et al. | 525/100 |
| 6,281,285 B1 | 8/2001 | Becker et al. | 524/837 |
| 6,307,083 B1 * | 10/2001 | Igarashi | 556/489 |
| 6,517,958 B1 | 2/2003 | Sellinger et al. | 428/690 |
| 6,605,373 B2 | 8/2003 | Woo et al. | |
| 6,616,863 B1 | 9/2003 | Angelopoulos et al. | 252/500 |
| 6,660,410 B2 * | 12/2003 | Hosokawa | 428/690 |
| 6,830,830 B2 | 12/2004 | Hsieh et al. | 428/690 |
| 6,897,473 B1 | 5/2005 | Burroughes et al. | 257/40 |
| 6,900,285 B2 | 5/2005 | Woo et al. | |
| 2001/0043043 A1 * | 11/2001 | Aoyama et al. | 313/506 |
| 2002/0149025 A1 | 9/2002 | Andriessen et al. | 257/98 |
| 2003/0120099 A1 | 3/2003 | Laine et al. | 556/450 |
| 2003/0204038 A1 | 10/2003 | Xiao et al. | 528/10 |
| 2003/0211358 A1 * | 11/2003 | Kitano et al. | 428/690 |
| 2004/0024164 A1 | 2/2004 | Lyu et al. | 528/10 |
| 2004/0209116 A1 | 10/2004 | Ren et al. | 428/690 |
| 2005/0035346 A1 | 2/2005 | Bazan et al. | 257/40 |
| 2005/0123760 A1 | 6/2005 | Cammack et al. | 428/403 |
| 2005/0142381 A1 * | 6/2005 | Lyu et al. | 428/690 |
| 2005/0212406 A1 | 9/2005 | Daniels et al. | 313/503 |
| 2007/0045619 A1 | 3/2007 | Park et al. | 257/40 |
| 2007/0112133 A1 | 5/2007 | Lee et al. | 525/100 |
| 2007/0138483 A1 | 6/2007 | Lee et al. | |

FOREIGN PATENT DOCUMENTS

| | | | |
|---|---|---|---|
| JP | 11003781 A * | 1/1999 | |
| JP | 11-329734 | 11/1999 | |
| JP | 2000-215987 | 8/2000 | |
| JP | 2004220931 A * | 8/2004 | |
| JP | 2006-108458 | 4/2006 | |
| KR | 2003-0097658 | 12/2003 | |
| KR | 2004-0056662 | 7/2004 | |
| KR | 2004-0070561 | 8/2004 | |
| KR | 2005-0032691 | 4/2005 | |
| KR | 2005-0056001 | 6/2005 | |

(Continued)

OTHER PUBLICATIONS

Müller et al. Acta Cryst. 2003, E59, o1838-o1839. Date of on-line publication: Oct. 31, 2003.*

(Continued)

*Primary Examiner*—D. Lawrence Tarazano
*Assistant Examiner*—Andrew K Bohaty
(74) *Attorney, Agent, or Firm*—Robert E. Bushnell, Esq.

(57) ABSTRACT

An organic light-emitting device including a first electrode, a second electrode, and an organic layer interposed between the first electrode and the second electrode. The organic layer includes at least one organosiloxane compound selected from organosiloxane compounds represented by $$M_2 -\!\!\left[L_3\right]_m\!\!-\!\!\left[\underset{B_4}{\underset{|}{\underset{B_3}{|}}} C = C \right]_l\!\!-L_1 - \underset{A_2}{\underset{|}{\overset{A_1}{\underset{|}{Si}}}} -\!\!\left[O - \underset{A_4}{\underset{|}{\overset{A_3}{\underset{|}{Si}}}}\right]_n\!\!- O - \underset{A_6}{\underset{|}{\overset{A_5}{\underset{|}{Si}}}} -$$

$$-L_2 -\!\!\left[\underset{B_2}{\underset{|}{\underset{B_1}{|}}} C = C \right]_l\!\!-\!\!\left[L_4\right]_m\!\!- M_1.$$

An organic light-emitting device using the organosiloxane compound has a low operating voltage, high color purity, and high efficiency.

11 Claims, 2 Drawing Sheets

FOREIGN PATENT DOCUMENTS

| KR | 2005-0077367 | 8/2005 |
| --- | --- | --- |
| WO | WO 95-01871 | 1/1995 |
| WO | WO 00/65653 | 11/2000 |

OTHER PUBLICATIONS

Machine translation of JP11-003781. Date of publication: Jan. 6, 1999.*

Machine translation of JP2004-220931. Date of publication: Aug. 5, 2004.*

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tri(3-methylphenylphenyl-amino)triphenylamine (m-MTDATA), as Hole-Transport Materials", Adv. Mater. 1994, 6, No. 9, pp. 677-679.

Wei-Jung Line et al., "Synthesis and Optoelectronic Properties of Starlike Polyfluorenes with a Silsesquioxane Core", Macromolecules 2004, 37, 2335-2341.

Chaobin He et al., "Highly Efficient Luminescent Organic Clusters with Quantum Dot-Like Properties", J. Am. Chem Soc. 2004, 126, 7792-7793.

Kalinowski, J., et al. "Injection-Controlled Electroluminescence in Organic Light-Emitting Diodes Based on Molecularly-Doped Polymers: II. Double-Layer Devices." J. Phys. D: Appl.Phys., vol. 34 (2001): pp. 2282-2295.

Rinaldi, A.W., et al. "Elecrical, Spectroscopic, and Thermal Properties of Blends Formed by PEDOT, PVC, and PEO." J. Appl. Poly. Sci., vol. 96 (2005); 1710-1715.

Ghosh, S., et al. "Supramolecular Self-Assembly for Enhanced Conductivity in Conjugated Polymer Blend: Ionic Crosslinking in Blends of Poly(3,4-ethylenedioxythiophene)-Poly(styrenesulfonate) and Poly(vinylpyrrolidone)." Adv. Mater., vol. 10, No. 14 (1998): pp. 1097-1099.

*Machine Translation* of JP 2006-108458.

*Machine Translation* of JP 2000-215987.

Kuwabara et al. "Thermally Stable Multilayered Organic Electroluminescent Devices Using Novel Starburst Molecules, 4,4'4"-Tri(N-carbazolyl)triphenylamine (TCTA) and 4,4'4"-Tri(3-methylphenylphenyl-amino) triphenylamine(m-MTDATA), as Hole-Transport Materials", Adv. Mater. 1994, 6, No. 9, pp. 677-679.

Chad M. Brick et al., "Robust Polyaromatic Octasilsesquioxanes from Polybromophenylsilsesquioxanes, BrxOPS, via Suzuki Coupling", Macromolecules 2005, 38, 4661-4665.

Office action from Chinese Patent Office issued in Applicant's corresponding Chinese Patent Application No. 200610153694.8 dated April 28, 2010, and its Request for Entry of the Accompanying Office Action.

Office Action issued by the Chinese Patent Office on Jul. 30, 2010 and Request for Entry of Accompanying Office Action herewith.

* cited by examiner

FIG. 1A

| SECOND ELECTRODE |
| --- |
| ELECTRON INJECTION LAYER |
| ELECTRON TRANSPORT LAYER |
| EMITTING LAYER |
| HOLE INJECTION LAYER |
| FIRST ELECTRODE |

FIG. 1B

| SECOND ELECTRODE |
| --- |
| ELECTRON INJECTION LAYER |
| ELECTRON TRANSPORT LAYER |
| EMITTING LAYER |
| HOLE TRANSPORT LAYER |
| HOLE INJECTION LAYER |
| FIRST ELECTRODE |

ORGANOSILOXANE COMPOUND AND ORGANIC LIGHT-EMITTING DEVICE COMPRISING THE SAME

CROSS-REFERENCE TO RELATED PATENT APPLICATIONS AND CLAIM OF PRIORITY

This application claims the benefit of Korean Patent Application No. 10-2005-0078720, filed on Aug. 26, 2005, in the Korean Intellectual Property Office, the disclosure of which is incorporated herein in its entirety by reference. Furthermore, the present application is related to two co-pending U.S. applications: 1) Ser. No. 11/480,876, entitled CONDUCTING POLYMER COMPOSITION AND ELECTRONIC DEVICE INCLUDING LAYER OBTAINED USING THE CONDUCTING POLYMER COMPOSITION based upon Korean Patent Application Serial No. 10-2005-0125455 filed in the Korean Intellectual Property Office on 19 Dec. 2005, and filed in the U.S. Patent & Trademark Office on 6 Jul. 2006; and 2) Ser. No. 11/517,480, entitled CONDUCTING POLYMER COMPOSITION AND ELECTRONIC DEVICE INCLUDING LAYER OBTAINED USING THE CONDUCTING POLYMER COMPOSITION based upon Korean Patent Application Serial No. 10-2005-0108523 filed in the Korean Intellectual Property Office on 14 Nov. 2005, and filed in the U.S. Patent & Trademark Office on 8 Sep. 2006.

BACKGROUND OF THE INVENTION

1. Field of the Invention

The present invention relates to an organosiloxane compound and an organic light-emitting device including the same, and more particularly, to an organosiloxane compound having high solubility and high thermal stability constituting a film having high thermal stability, and an organic light-emitting device having a low operating voltage, high efficiency, and high color purity including the organosiloxane compound.

2. Description of the Related Art

Light-emitting devices are self-emission type devices and have wide viewing angles, excellent contrast, and short response times. Organic light-emitting devices can be categorized into inorganic light-emitting devices having emitting layers formed of inorganic compounds and organic light-emitting devices (OLEDs) having emitting layers formed of organic compounds. OLEDs have high brightness, low operating voltages, and short response times, and can realize various colors, compared to inorganic light-emitting devices. As a result, a lot of research into OLEDs is being conducted.

In general, an OLED has an anode/organic emitting layer/cathode structure. However, an OLED can have various structures, such as an anode/hole injection layer/hole transport layer/emitting layer/electron transport layer/electron injection layer/cathode structure, an anode/hole injection layer/hole transport layer/emitting layer/hole blocking layer/electron transport layer/electron injection layer/cathode structure, or the like.

Materials used to manufacture OLEDs can be categorized into vacuum deposition materials and solution coating materials, according to a method of forming an organic layer. A vacuum deposition material should have a vapor pressure of $10^{-6}$ torr or higher, and can be a small molecular material having a molecular weight of 1200 or less. A solution coating material should have high solubility with respect to a solvent such that it can be prepared in a liquid state, and can be aromatic or polycyclic material.

When an OLED is manufactured using a vacuum deposition method, a vacuum system is required and thus manufacturing costs increase, and when a shadow mask is used to define a pixel used for displaying natural color, it is difficult to obtain a pixel having high resolution. On the other hand, a solution coating method, such as an inkjet printing method, a screen printing method, or a spin coating method, can be easily used, is inexpensive, and can be used to obtain a relatively higher pixel resolution than when a shadow mask is used.

However, among materials that can be used in a solution coating method, blue light-emitting molecules exhibit inferior thermal stability and color purity compared to materials that can be used in a vacuum deposition method. In addition, even when blue light-emitting molecules have high thermal stability and high color purity are used, an organic layer formed of the blue light-emitting molecules is gradually crystallized such that visible rays are dispersed, a whitening effect takes place, and pinholes can be formed, since the size of the formed crystals corresponds to a wavelength of visible light. Thus a device may easily deteriorate.

For example, U.S. Pat. No. 4,672,265 discloses a compound having π electron system susceptible to external perturbation and can be excited by electric field. However, the compound exhibits low heat resistance stability. U.S. Pat. No. 6,307,083 discloses specific organic silane compounds. The specific organic silane compounds have high solubility with respect to a solvent but a film formed of the organic silane compound using a solution coating method exhibits bad film quality and an organic light-emitting device including the film formed of the organic silane compound exhibits inferior performance.

Accordingly, there is a need to develop an organic light-emitting device having a low operating voltage, high brightness, high efficiency, and high color purity using a blue light-emitting compound having good thermal stability constituting an organic layer having good film quality.

SUMMARY OF THE INVENTION

The present invention provides an organosiloxane compound containing a siloxane group.

The present invention also provides an organic light-emitting device having a low operating voltage, high efficiency, and high color purity.

According to an aspect of the present invention, there is provided an organosiloxane compound represented by Formula 1:

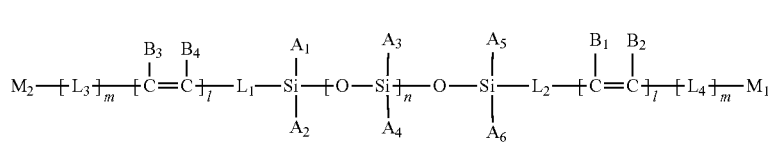

<Formula 1> where $L_1$, $L_2$, $L_3$, and $L_4$ are each independently a substituted or unsubstituted $C_6$-$C_{30}$ arylene group, or a substituted or unsubstituted $C_2$-$C_{30}$ heteroarylene group;

$M_1$ and $M_2$ are each independently

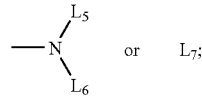

$L_5$, $L_6$, and $L_7$ are each independently a substituted or unsubstituted $C_6$-$C_{30}$ aryl group, or a substituted or unsubstituted $C_2$-$C_{30}$ heteroaryl group, and $L_5$ and $L_6$ are optionally connected to form a substituted or unsubstituted ring having the N atom;

$A_1$, $A_2$, $A_3$, $A_4$, $A_5$, and $A_6$ are each independently hydrogen, a substituted or unsubstituted $C_1$-$C_{20}$ alkyl group, a substituted or unsubstituted $C_1$-$C_{20}$ alkoxy group, or a substituted or unsubstituted $C_6$-$C_{30}$ aryl group;

$B_1$, $B_2$, $B_3$, and $B_4$ are each independently hydrogen, a substituted or unsubstituted $C_1$-$C_{20}$ alkyl group, or a substituted or unsubstituted $C_6$-$C_{30}$ aryl group;

n is an integer of 0 through 5;
l is an integer of 0 or 1; and
m is an integer of 0 through 3.

According to another aspect of the present invention, there is provided an organic light-emitting device including: a first electrode; a second electrode; and an organic layer containing the organosiloxane compound interposed between the first electrode and the second electrode.

Compared to a conventional organic light-emitting device having an organic layer having weak deterioration resistance formed using a solution coating method, the organic light-emitting device according to the present invention includes an organosiloxane compound having high solubility and high thermal stability constituting an organic layer having strong deterioration resistance, and provides a low operating voltage, high efficiency, and high color purity.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein:

FIGS. 1A through 1C are sectional views of organic light-emitting devices according to embodiments of the present invention.

DETAILED DESCRIPTION OF THE INVENTION

Figure 1C:
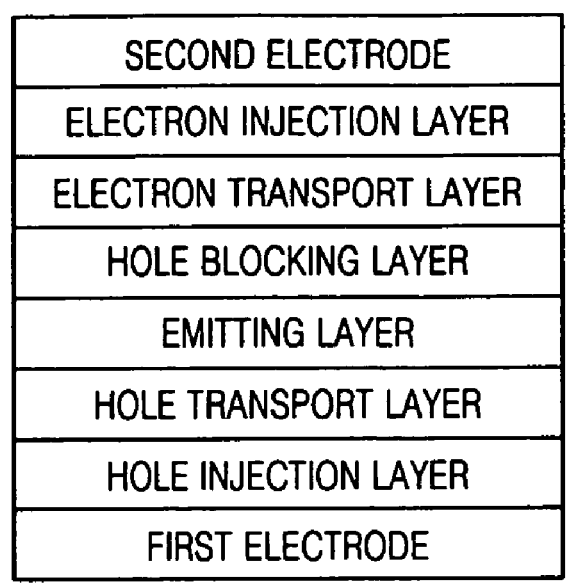

The present invention will now be described more fully with reference to the accompanying drawings.

An organosiloxane compound according to an embodiment of the present invention is represented by Formula 1:

where $L_1$, $L_2$, $L_3$, and $L_4$ are each independently a substituted or unsubstituted $C_6$-$C_{30}$ arylene group, or a substituted or unsubstituted $C_2$-$C_{30}$ heteroarylene group;

$M_1$ and $M_2$ are each independently

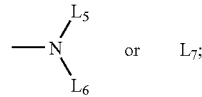

$L_5$, $L_6$, and $L_7$ are each independently a substituted or unsubstituted $C_6$-$C_{30}$ aryl group, or a substituted or unsubstituted $C_2$-$C_{30}$ heteroaryl group, and $L_5$ and $L_6$ may be connected to form a substituted or unsubstituted ring having the N atom (i.e., $L_5$ and $L_6$ are optionally connected);

$A_1$, $A_2$, $A_3$, $A_4$, $A_5$, and $A_6$ are each independently hydrogen, a substituted or unsubstituted $C_1$-$C_{20}$ alkyl group, a substituted or unsubstituted $C_1$-$C_{20}$ alkoxy group, or a substituted or unsubstituted $C_6$-$C_{30}$ aryl group;

$B_1$, $B_2$, $B_3$, and $B_4$ are each independently hydrogen, a substituted or unsubstituted $C_1$-$C_{20}$ alkyl group, or a substituted or unsubstituted $C_6$-$C_{30}$ aryl group;

n is an integer of 0 through 5;
l is an integer of 0 or 1; and
m is an integer of 0 through 3.

In Formula 1, H can be substituted. More particular, a substituent of the alkyl group, the aryl group, the heteroaryl group, and the cycloalkyl group may include at least one selected from the group consisting of —F; —Cl; —Br; —CN; —NO$_2$; —OH; an unsubstituted $C_1$-$C_{20}$ alkyl group; a $C_1$-$C_{20}$ alkyl group substituted with —F, —Cl, —Br, —CN, —NO$_2$, or —OH; an unsubstituted $C_1$-$C_{20}$ alkoxy group; a $C_1$-$C_{20}$ alkoxy group substituted with —F, —Cl, —Br, —CN, —NO$_2$, or —OH; an unsubstituted $C_6$-$C_{30}$ aryl group; a $C_6$-$C_{30}$ aryl group substituted with —F, —Cl, —Br, —CN, —NO$_2$, or —OH; an unsubstituted $C_2$-$C_{30}$ heteroaryl group; a $C_2$-$C_{30}$ heteroaryl group substituted with —F, —Cl, —Br, —CN, —NO$_2$, or —OH; an unsubstituted $C_5$-$C_{20}$ cycloalkyl group; and a $C_5$-$C_{20}$ cycloalkyl group substituted with —F, —Cl, —Br, —CN, —NO$_2$, or —OH. However, the substituent of the alkyl group, the aryl group, the heteroaryl group, and the cycloalkyl group is not limited thereto.

Particularly, in Formula 1, $L_1$, $L_2$, $L_3$, and $L_4$ may be each independently a phenylene group, a $C_1$-$C_{10}$ alkylphenylene group, a $C_1$-$C_{10}$ alkoxyphenylene group, a halophenylene group, a cyanophenylene group, a dicyanophenylene group, a trifluoromethoxyphenylene group, an o-, m-, or p-tolylene group, an o-, m-, or p-cumenylene group, a mesitylene group, a phenoxyphenylene group, an (α,α-dimethylbenzene)phenylene group, a (N,N'-dimethyl)aminophenylene group, a (N, N'-diphenyl)aminophenylene group, a ($C_1$-$C_{10}$ alkylcyclohexyl)phenylene group, an (anthracenyl)phenylene group, a biphenylene group, a $C_1$-$C_{10}$ alkylbiphenylene group, a $C_1$-$C_{10}$ alkoxybiphenylene group, a pentalenylene group, an indenylene group, a naphthylene group, a $C_1$-$C_{10}$ alkyl naphthylene group, a $C_1$-$C_{10}$ alkoxynaphthylene group, a halonaphthylene group, a cyanonaphthylene group, a biphenylenylene group, a $C_1$-$C_{10}$ alkyl biphenylene group, a

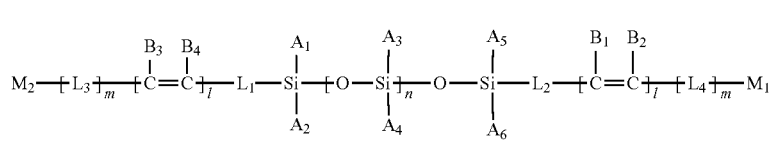

<Formula 1>

$C_1$-$C_{10}$ alkoxy biphenylene group, an anthracenylene group, an azulenylene group, a heptalenylene group, an acenaphthylenylene group, a phenalenylene group, a fluorenylene group, an anthraquinolylene group, a methylanthrylene group, a phenanthrenylene group, a triphenylenylene group, a pyrenylene group, a chrysenylene group, an ethyl-chrysenylene group, a picenylene group, a perylenylene group, a chloroperylenylene group, a pentaphenylene group, a pentacenylene group, a tetraphenylenylene group, a hexaphenylene group, a hexacenylene group, a rubicenylene group, a coronenylene group, a trinaphthylenylene group, a heptaphenylene group, a heptacenylene group, a pyranthrenylene group, an ovalenylene group, a carbazolylene group, a $C_{1-10}$ alkyl carbazolylene group, a thio phenylene group, an indolylene group, purinylene group, a benzimidazolylene group, a quinolinylene group, a benzothiophenylene group, a para thiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridinylene group, a pyridazinylene group, a pyrimidinylene group, a pyrazinylene group, a thianthrenylene group, a pyrrolidinylene group, a pyrazolidinylene group, an imidazolidinylene group, a piperidinylene group, a piperazinylene group, or a morpholynylene group. However, $L_1$, $L_2$, $L_3$, and $L_4$ are not limited thereto. $L_1$, $L_2$, $L_3$, and $L_4$ may be the same or different.

Preferably, $L_1$, $L_2$, $L_3$, and $L_4$ are each independently a substituted or unsubstituted phenylene group, a substituted or unsubstituted naphthalene group, a substituted or unsubstituted anthracene group, a substituted or unsubstituted phenanthrene group, a substituted or unsubstituted fluorene group, a substituted or unsubstituted carbazoyl group, a substituted or unsubstituted thiophene group, or a substituted or unsubstituted thiazole group.

In Formula 1, $M_1$ and $M_2$ are each independently

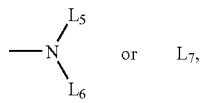

and $L_5$ and $L_6$ may be connected to form a substituted or unsubstituted ring containing an N atom. The ring may or may not have an orientation.

In Formula 1, $L_5$, $L_6$, and $L_7$ may be each independently a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl group, an o-, m-, or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a ($C_1$-$C_{10}$ alkylcyclohexyl) phenyl group, an (anthracenyl)phenyl group, biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenyl group, a $C_1$-$C_{10}$ alkoxy biphenyl group, an anthracenyl group, an azulenyl group, a heptalenyl group, an acenaphthylenyl group, a phenalenyl group, a fluorenyl group, an anthraquinolyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a $C_{1-10}$ alkyl carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a pyrrolidinyl group, a pyrazolidinyl group, an imidazolidinyl group, a piperidinyl group, a piperazinyl group, a carbazoryl group, a bezoxazolyl group, a phenothiazinyl group, a 5H-dibenzazepinyl group, a 5H-tribenzazepinyl group, or a morpholinyl group. However, $L_5$, $L_6$, and $L_7$ are not limited thereto. $L_5$, $L_6$, and $L_7$ may be all the same or different.

Preferably, $L_5$, $L_6$, and $L_7$ are each independently a substituted or unsubstituted phenyl group, a substituted or unsubstituted naphthyl group, a substituted or unsubstituted anthracenyl group, or a substituted or unsubstituted phenanthrenyl group. More preferably, $L_5$, $L_6$, and $L_7$ are each independently phenyl group, naphthyl, biphenyl, anthracenyl, phenanthrenyl, pyridinyl, benzothiophenyl, thianthrenyl, carbazolyl, benzoxazolyl, phenothiazolyl, 5H-dibenzazepinyl, 5H-tribenzazepinyl, or propylcyclohexyl.

In Formula 1, $A_1$, $A_2$, $A_3$, $A_4$, $A_5$, and $A_6$ are each independently hydrogen, a methyl group, an ethyl group, a propyl group, a butyl group, a methoxy group, an ethoxy group, a propoxy group, a butoxy group, a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a ($C_1$-$C_{10}$ alkylcyclohexyl)phenyl group, an (anthracenyl)phenyl group, a biphenyl group, $C_1$-$C_{10}$ alkylbiphenyl group, a $C_1$-$C_{10}$ alkoxybiphenyl group, a pentalenyl group, indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenyl group, a $C_1$-$C_{10}$ alkoxy biphenyl group, an anthracenyl group, azulenyl group, a heptarenyl group, an acenaphthylenyl group, a phenalenyl group, a fluorenyl group, an anthraquinolyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptarenyl group, a pyranthrenyl group, an ovalenyl group, a carbazolyl group, a cyclopentyl group, a cyclohexyl group, a $C_1$-$C_{10}$ alkylcyclohexyl group, or a $C_1$-$C_{10}$ alkoxycyclohexyl group. However, $A_1$, $A_2$, $A_3$, $A_4$, $A_5$, and $A_6$ are not limited thereto. $A_1$, $A_2$, $A_3$, $A_4$, $A_5$, and $A_6$ may be all the same or different.

In Formula 1, $B_1$, $B_2$, $B_3$, and $B_4$ are each independently hydrogen, methyl, ethyl, propyl, butyl, a phenyl group, a $C_1$-$C_{10}$ alkylphenyl group, a $C_1$-$C_{10}$ alkoxyphenyl group, a halophenyl group, a cyanophenyl group, a dicyanophenyl group, a trifluoromethoxyphenyl group, an o-, m-, or p-tolyl group, an o-, m-, or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a ($C_1$-$C_{10}$ alkylcyclohexyl)phenyl group, an (anthracenyl)phenyl group, a biphenyl group, a $C_1$-$C_{10}$ alkylbiphenyl group, a $C_1$-$C_{10}$ alkoxybiphenyl group, a pentalenyl group, an indenyl group, a naphthyl group, a $C_1$-$C_{10}$ alkylnaphthyl group, a $C_1$-$C_{10}$ alkoxynaphthyl group, a halonaphthyl group, a cyanonaphthyl group, a biphenylenyl group, a $C_1$-$C_{10}$ alkyl biphenyl group, a $C_1$-$C_{10}$ alkoxy biphenyl group, an anthracenyl group, an azulenyl group, a heptarenyl group, an acenaphthylenyl group, a phenalenyl group, a fluorenyl group, an anthraquinolyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a cyclopentyl group, a cyclohexyl group, a $C_1$-$C_{10}$ alkylcyclohexyl group, or a $C_1$-$C_{10}$ alkoxycyclohexyl group. However, $B_1$, $B_2$, $B_3$, and $B_4$ are not limited thereto. $B_1$, $B_2$, $B_3$, and $B_4$ may be all the same or different.

The organosiloxane compound according to an embodiment of the present invention can be represented by Formulae 2 through 25, but is not limited thereto:

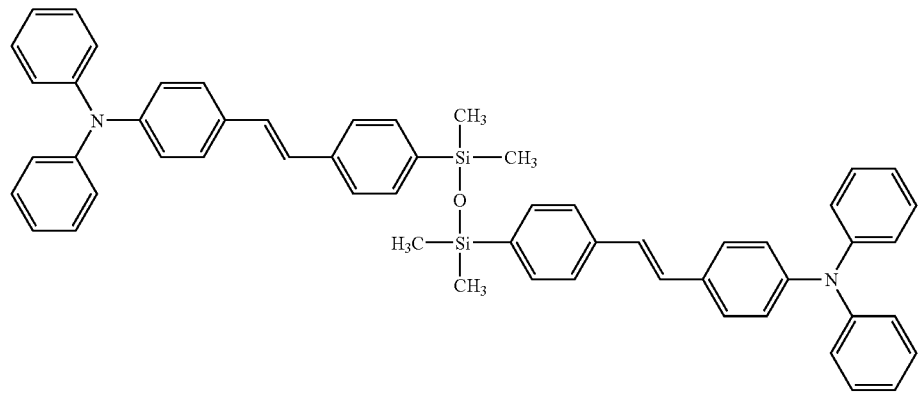

<Formula 2>

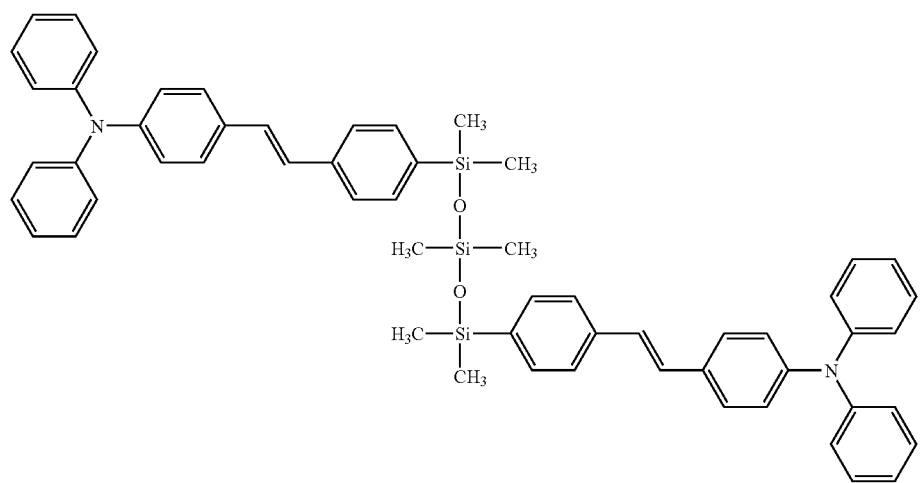

<Formula 3>

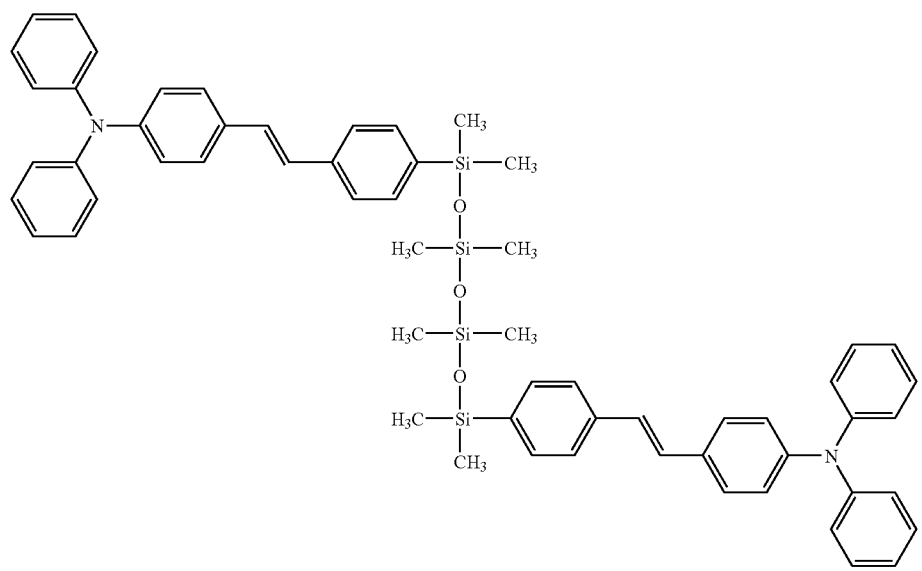

<Formula 4>

-continued
<Formula 5>
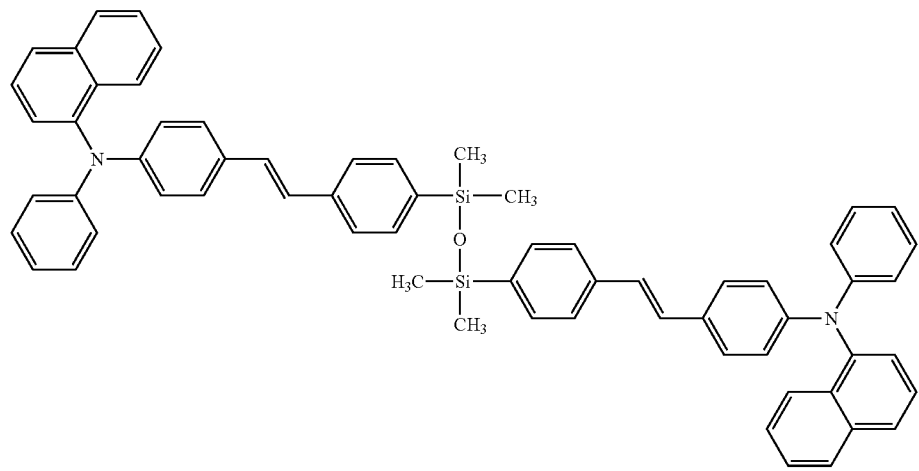
<Formula 6>
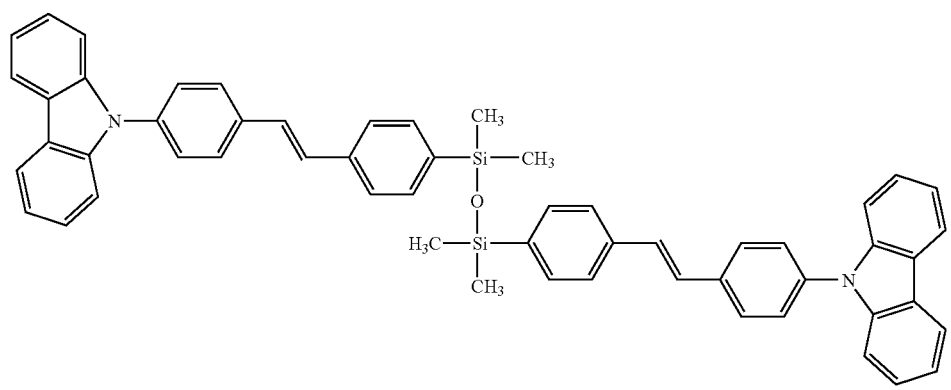
<Formula 7>
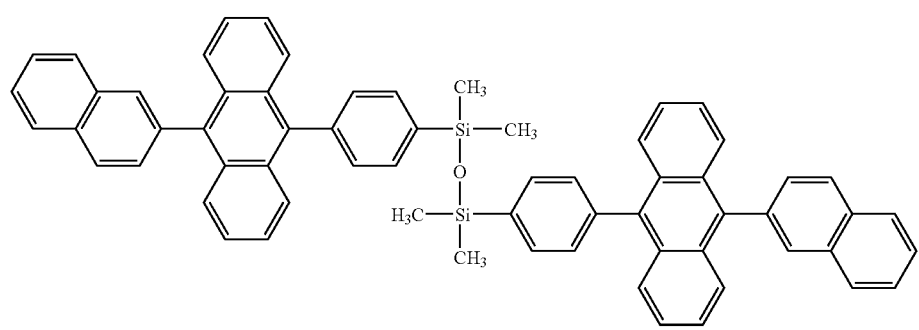
<Formula 8>
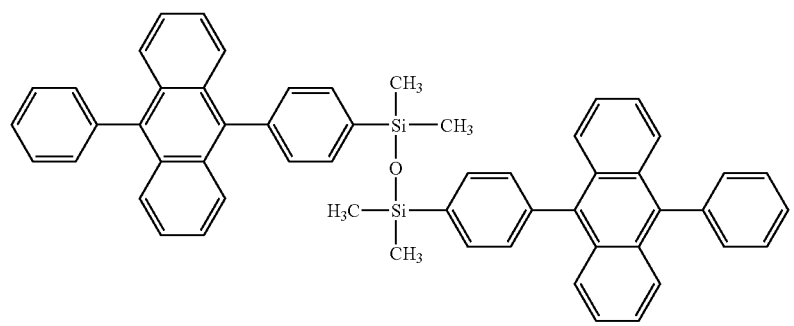

-continued
<Formula 9>
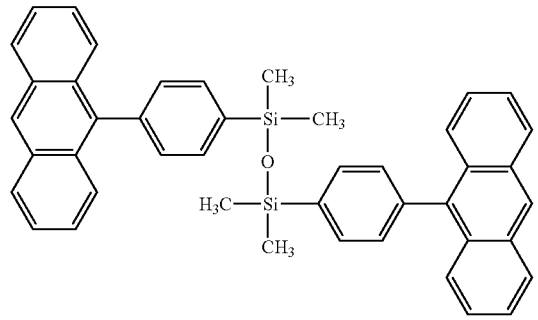
<Formula 10>
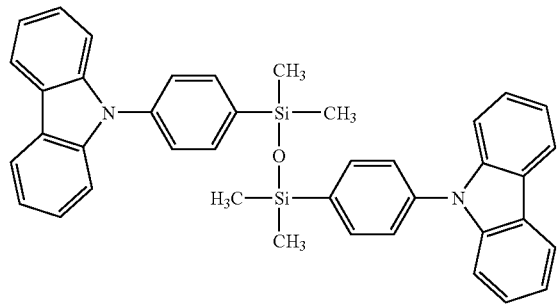
<Formula 11>
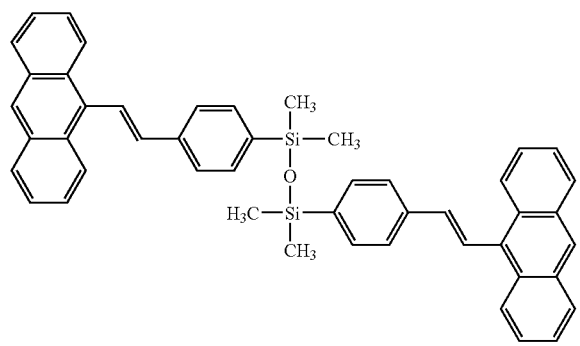
<Formula 12>
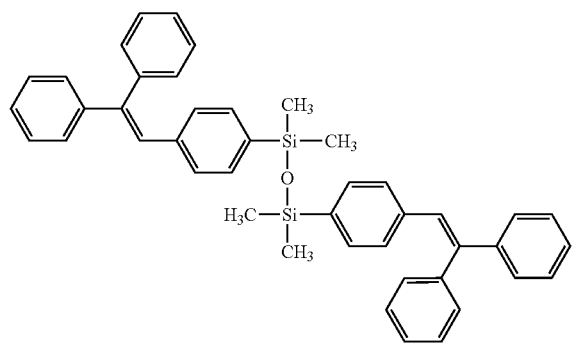
<Formula 13>
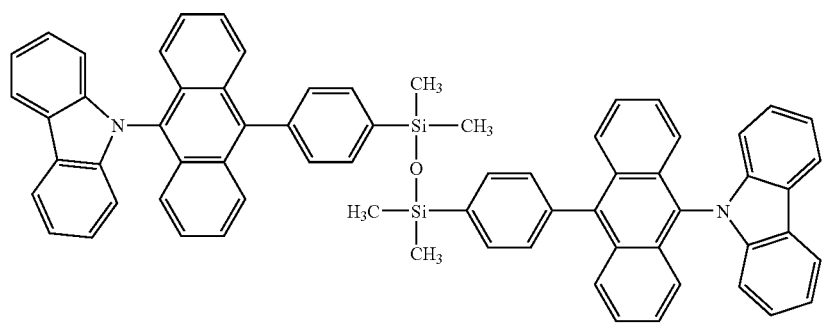
<Formula 14>
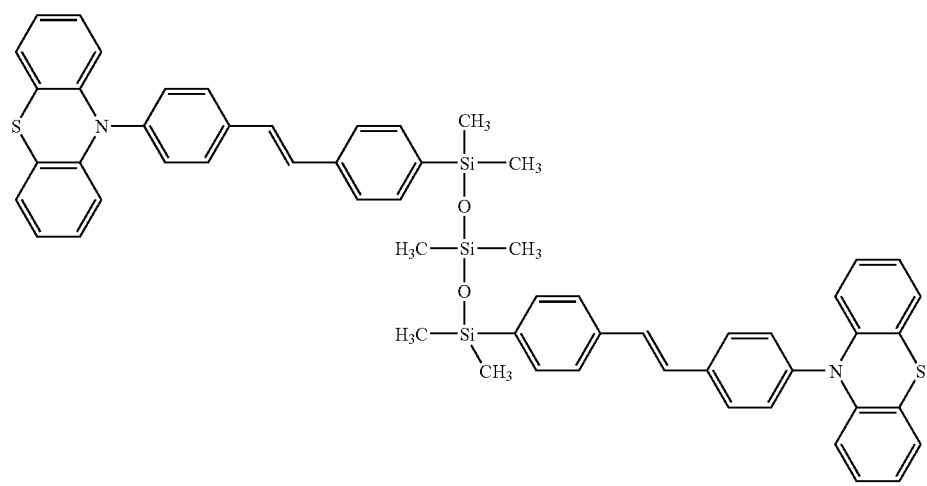

<Formula 15>
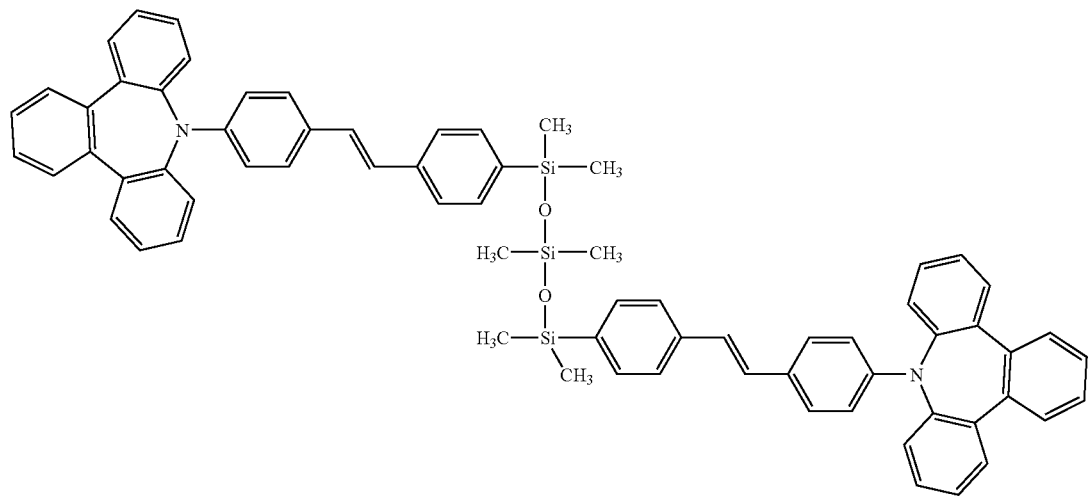
<Formula 16>
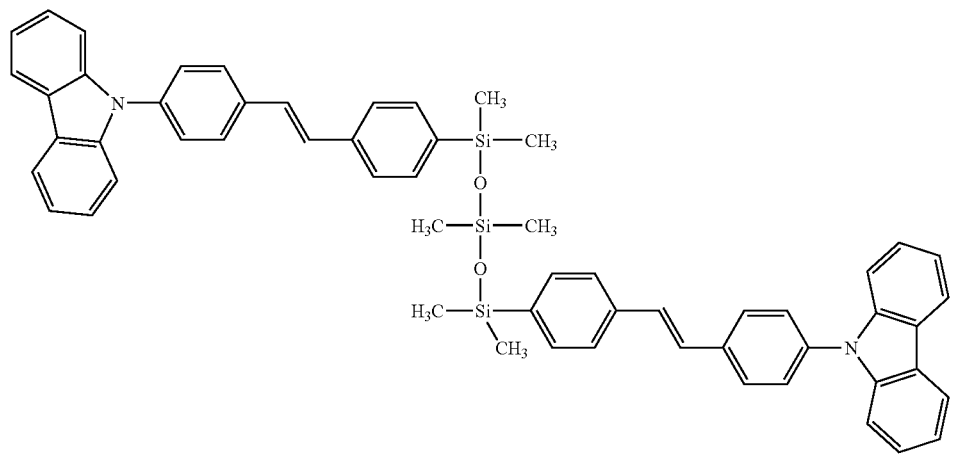
<Formula 17>
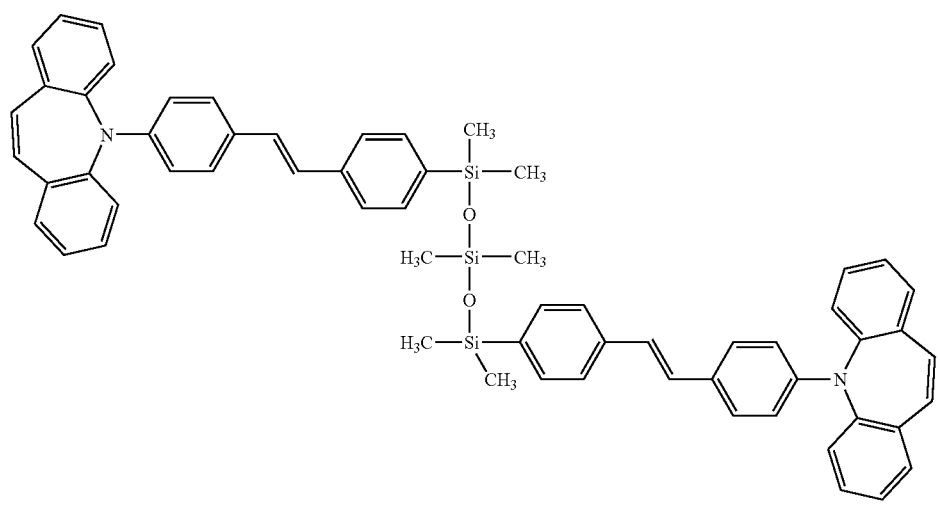

-continued
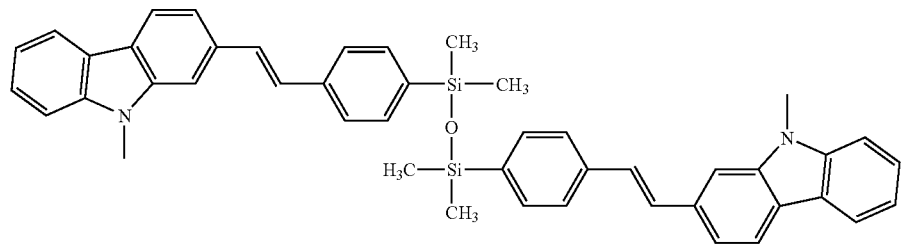
<Formula 18>
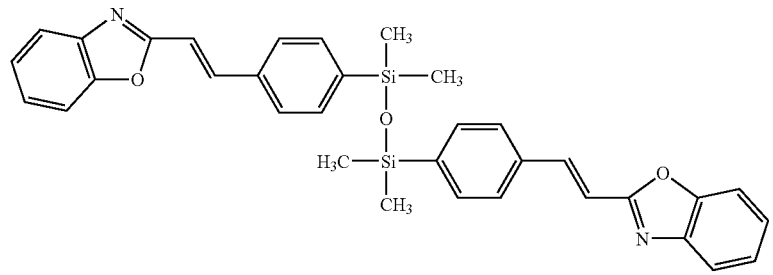
<Formula 19>
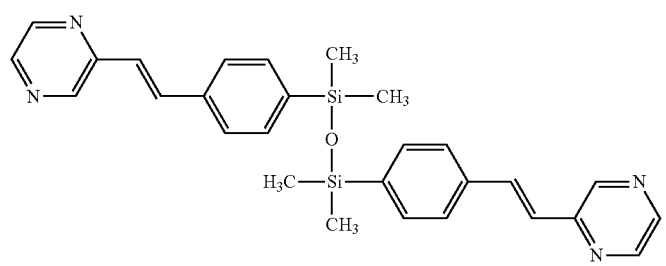
<Formula 20>
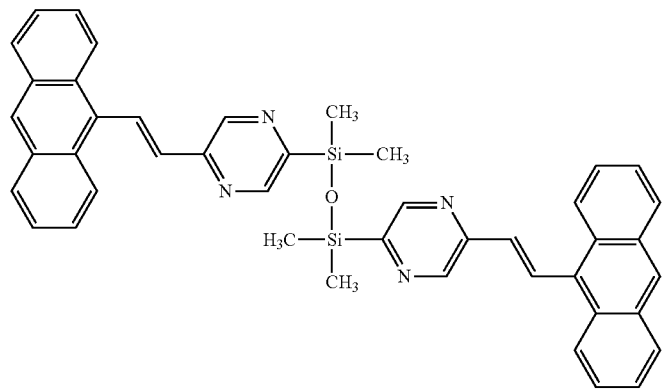
<Formula 21>
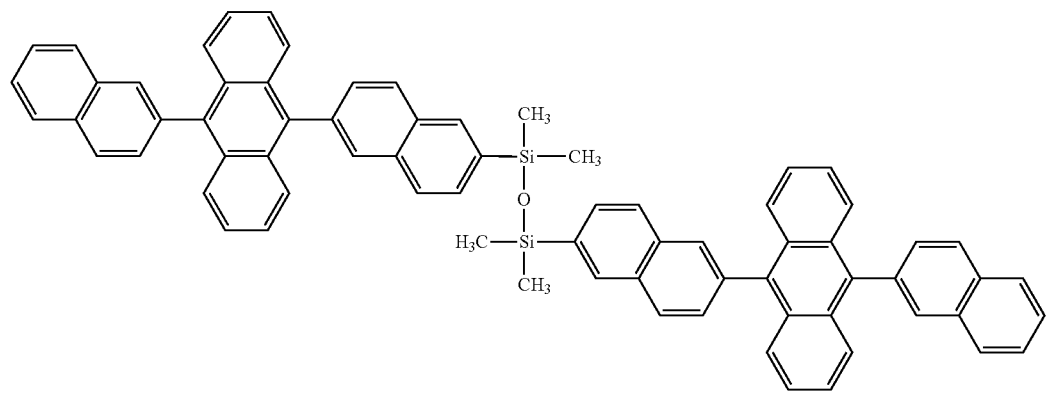
<Formula 23>

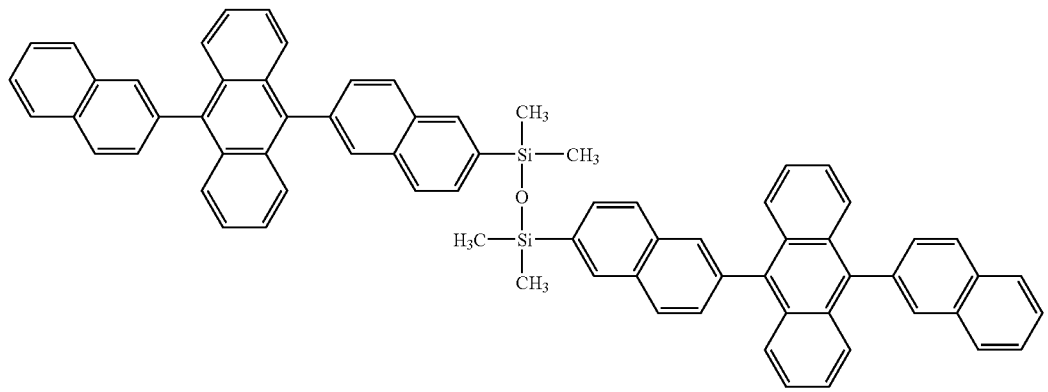

<Formula 23>

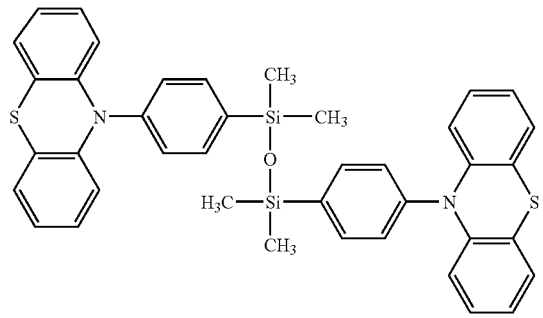

<Formula 24>

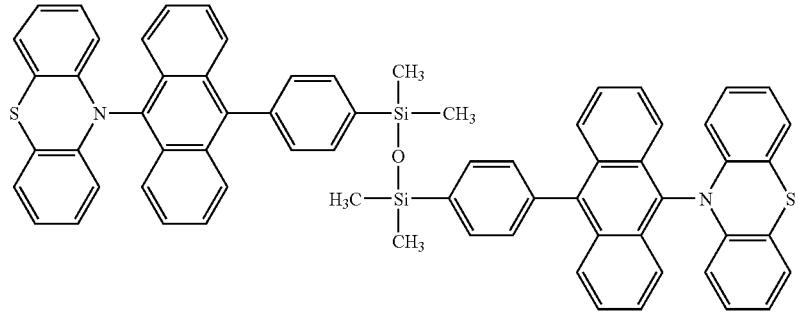

<Formula 25>

An organic light-emitting device according to an embodiment of the present invention includes a first electrode, a second electrode, and an organic layer interposed between the first electrode and the second electrode. The organic layer may include at least one organosiloxane compound represented by Formula 1, preferably Formula 2 through 25.

An organosiloxane compound represented by one of Formulae 1 through 25 includes aryl group, vinyl group, or hetero aryl group, and a siloxane group that is a polar functional group. Accordingly, the organosiloxane compound has high solubility with respect to a solvent, and a device using the organosiloxane compound may have a low operating voltage and high efficiency. Due to these advantages, an organic layer including the organosiloxane compound represented by Formulae 1 through 25 can be used as an emitting layer or a hole transport layer.

The organic light-emitting device according to an embodiment of the present invention may have various structures. For example, the organic light-emitting device may include a first electrode, a second electrode, an emitting layer and optionally at least one layer selected from a hole injection layer, a hole transport layer, an electron blocking layer, a hole blocking layer, an electron transport layer, and an electron injection layer interposed between the first electrode and the second electrode.

Organic light-emitting devices according to embodiments of the present invention are illustrated in FIGS. 1A, 1B, and 1C. FIG. 1A is a sectional view of an organic light-emitting device having a first electrode/hole injection layer/emitting layer/electron transport layer/electron injection layer/second electrode structure. FIG. 1B is a sectional view of an organic light-emitting device having a first electrode/hole injection layer/hole transport layer/emitting layer/electron transport layer/electron injection layer/second electrode structure. FIG. 1C is a sectional view of an organic light-emitting device having a first electrode/hole injection layer/hole transport layer/emitting layer/hole blocking layer/electron transport layer/electron injection layer/second electrode structure. In these embodiments, the emitting layer may include an organosiloxane compound according to an embodiment of the present invention.

An emitting layer of an organic light-emitting device according to an embodiment of the present invention may contain a phosphorescent or fluorescent dopant which emits red, green, blue, or white light. The phosphorescent dopant may include at least one organometallic compound selected from Ir, Pt, Os, Ti, Zr, Hf, Eu, Tb, and Tm.

An exemplary method of manufacturing an organic light-emitting device according to an embodiment of the present invention will now be described with reference to the organic light-emitting device illustrated in FIG. 1C.

First, a high work function first electrode material is deposited on a substrate using a depositing method or a sputtering method to form a first electrode. The first electrode can be an anode. The substrate may be a substrate that is commonly used in a conventional organic light emitting display device. For example, the substrate may be a glass substrate or a transparent plastic substrate, both of which have mechanical strength, thermal stability, and plane surfaces, are transparent and waterproof, and can be easily handled. The first electrode material may be a conductive transparent material, such as indium tin oxide (ITO), indium zinc oxide (IZO), tin oxide ($SnO_2$), zinc oxide (ZnO), and the like.

Then, a hole injection layer (HIL) can be formed on the first electrode using various methods, such as a vacuum depositing method, a spin coating method, a casting method, a LB method, or the like.

When the HIL is formed by vacuum deposition, deposition conditions may vary according to HIL forming compounds and the structure and thermal properties of a HIL which will be formed. For example, a deposition temperature may be in the range of 100 to 500° C., a pressure may be in the range of $10^{-8}$ to $10^{-3}$ torr, a deposition rate may be in the range of 0.01 to 100 Å/sec, and a thickness of the HIL may be in the range of 10 Å to 5 μm.

When the HIL is formed by spin coating, coating conditions may vary HIL forming compounds and the structure and thermal properties of a HIL which will be formed. A coating speed may be in the range of about 2000 rpm to 5000 rpm, and a heat treatment temperature for removing a solvent after the coating may be in the range of about 80° C. to 200° C.

The HIL forming material is not be limited, and may be a phthalocyanine compound, such as copper phthalocyanine disclosed in U.S. Pat. No. 4,356,429; a starburst type amine derivative, such as TCTA, m-MTDATA, and m-MTDAPB, disclosed in Advanced Material, 6, p. 677 (1994); or a conductive soluble polymer, such as polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

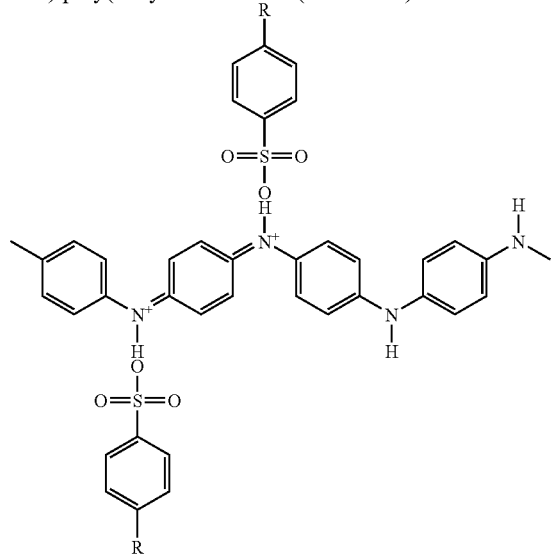

Pani/DBSA

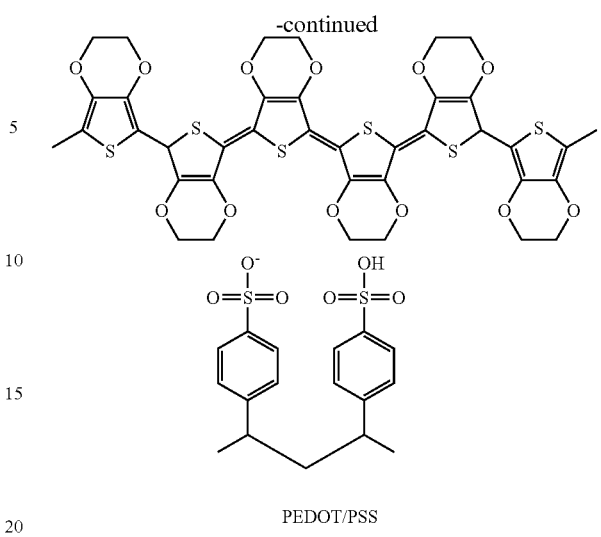

PEDOT/PSS

The thickness of the HIL may be in the range of about 100 Å to 10000 Å, preferably 100 Å to 1000 Å. When the thickness of the HIL is less than 100 Å, a hole injecting property may decrease. On the other hand, when the thickness of the HIL is greater than 10000 Å, the operating voltage may increase.

Subsequently, a hole transport layer (HTL) can be formed on the HIL by vacuum deposition, spin coating, casting, LB, or the like. When the HTL is formed by vacuum deposition or spin coating, vacuum deposition conditions or spin coating conditions may vary according to HTL forming compounds and may be the same as when the HIL is formed.

The HTL forming material is not limited, and may be selected from known HTL forming materials. For example, the HTL forming material may be a carbazole derivative, such as N-phenylcarbazole, polyvinylcarbazole, or the like; or a conventional amine derivative having an aromatic condensation ring, such as N,N'-bis(3-methylphenyl)-N,N'-diphenyl-[1,1-biphenyl]-4,4'-diamine (TPD), N,N'-di(naphthalene-1-yl)-N,N'-diphenyl benxidine (α-NPD), or the like.

The thickness of the HTL may be in the range of about 50-1000 Å, preferably, 100 Å to 600 Å. When the thickness of the HTL is less than 50 Å, properties of the HTL may deteriorate. On the other hand, when the thickness of the HTL is greater than 1000 Å, the operating voltage may increase.

Then, an emitting layer (EML) can be formed on the HTL by vacuum depositing, spin coating, casting, LB, or the like. When the EML is formed by vacuum deposition or spin coating, vacuum deposition conditions or spin coating conditions may vary according to EML forming compounds and may be almost the same as when the HIL is formed.

The EML may include an aminostyryl compound of Formula 1, as described above. The aminostyryl compound of Formula 1 can be used together with a proper known host material. The host material can be, for example, $Alq_3$, CBP (4,4'-N,N'-dicarbazole-biphenyl), or PVK(poly(n-vinylcarbazole)).

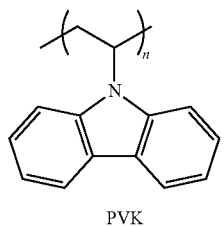

PVK

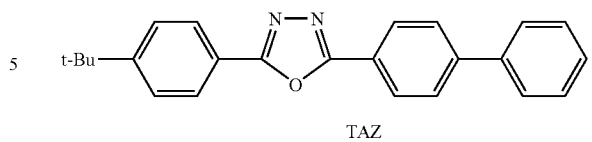

TAZ

Meanwhile, as the EML forming material, other dopants, in addition to the aminostyryl compound according to an embodiment of the present invention, can be used. For example, a fluorescent dopant can be IDE102 or IDE105 (produced by Idemitsu Kosan Co., Ltd.), or C545T (produced by Hayashibara Inc.); and a phosphorescent dopant can be PtOEP or RD 61 (produced by UDC Inc.) as a red phosphorescent dopant, Ir(PPy)$_3$(PPy=2-phenylpyridine) as a green phosphorescent dopant, and F2Irpic as a blue phosphorescent dopant.

The concentration of the dopant used is not limited, and may be in the range of 0.01 to 15 parts by weight based on 100 parts by weight of a host.

The thickness of the EML may be in the range of 100-800 Å, preferably, 300-400 Å. When the thickness of the EML is less than 100 Å, efficiency and lifetime of the device are reduced. On the other hand, when the thickness of the EML is greater than 800 Å, the operating voltage increases.

The thickness of the EML may be in the range of 100-1000 Å, preferably, 200-600 Å. When the thickness of the EML is less than 100 Å, a luminous property may deteriorate. On the other hand, when the thickness of the EML is greater than 1000 Å, the operating voltage may increase.

When the EML is formed using a phosphorescent dopant, a hole blocking layer (HBL) can be formed on the HTL using a vacuum deposition method, a spin coating method, a casting method, LB, or the like to prevent diffusion of triple excimers or holes into an electron transport layer. When the HBL is formed by vacuum deposition and spin coating, the vacuum deposition conditions or spin coating conditions may vary according to HBL forming compounds and may be almost the same as when the HIL is formed. A known, available hole blocking material can be, for example, an oxadiazole derivative, a triazole derivative, a phenanthroline derivative, a hole blocking material disclosed in JP 11-329734(A1), BCP, or the like.

The thickness of the HBL may be in the range of about 50 Å to 1000 Å, for example, 100 Å to 300 Å. When the thickness of the HBL is less than 50 Å, a hole blocking property may decrease. On the other hand, when the thickness of the HBL is greater than 1000 Å, the operating voltage may increase.

Subsequently, an electron transport layer (ETL) can be formed using a vacuum deposition method, a spin coating method, a casting method, or the like. When the ETL is formed by vacuum deposition or spin coating, the vacuum deposition conditions or spin coating conditions may vary according to ETL forming compounds and may be almost the same as when the HIL is formed. The ETL forming compound stably transports electrons injected from an electron injection electrode (cathode) and can be a quinoline derivative, such as tris(8-quinolinolate)aluminum(Alq$_3$) or TAZ.

The thickness of the ETL may be in the range of about 100 Å-1000 Å, preferably, 200 Å-500 Å. When the thickness of the ETL is less than 100 Å, an electron transporting property may decrease. On the other hand, when the thickness of the ETL is greater than 1000 Å, the operating voltage may increase.

An electron injection layer (EIL), which allows easy injection of electrons from a cathode, can be formed on the ETL. An EIL forming material is not limited.

The EIL can be formed of any known EIL forming material, such as LiF, NaCl, CsF, Li$_2$O, BaO, or the like. Conditions for depositing an EIL may vary according to EIL forming materials and may be almost the same as when the HIL is formed.

The thickness of the EIL may be in the range of about 1 Å-100 Å, preferably, 5 Å to 50 Å. When the thickness of the EIL is less than 1 Å, an electron injecting property may decrease. On the other hand, when the thickness of the EIL is greater than 100 Å, the operating voltage may increase.

Subsequently, a second electrode can be formed on the EIL using a vacuum deposition method or a sputtering method. The second electrode can be used as a cathode. A second electrode forming metal can be a metal, an alloy, an electrically conductive compound, and a mixture of these, which has a low work function. For example, the second electrode forming metal is Li, Mg, Al, Al—Li, Ca, Mg—In, Mg—Ag, or the like. Meanwhile, in order to obtain a front emission type light-emitting device, the cathode can be formed of a transparent material, such as ITO or IZO.

An organic light-emitting device according to an embodiment of the present invention may have various structures, in addition to the structure of an organic light-emitting device including a first electrode, a HIL, a HTL, an EML, a HBL, an ETL, an EIL, and a second electrode illustrated in FIG. 1C. For example, the organic light-emitting device according to an embodiment of the present invention can be an organic light-emitting device illustrated in FIG. 1A, which will be described in detail in Examples.

The organosiloxane compound of Formula 1 was prepared according to a conventional organic synthesis method. Synthesis products were determined using 1H NMR, and Mass Spectrometer.

Hereinafter, Synthesis Examples and Examples for preparing Compounds 2 through 12 respectively represented by Formulae 2 through 12 (hereinafter, referred to as "Compound 2" through "Compound 12" according to the present invention will be described in detail. However, the present invention is not limited to Synthesis Examples and Examples.

SYNTHESIS EXAMPLES

Methods of synthesizing Intermediates that are used to prepare respective compounds will now be described

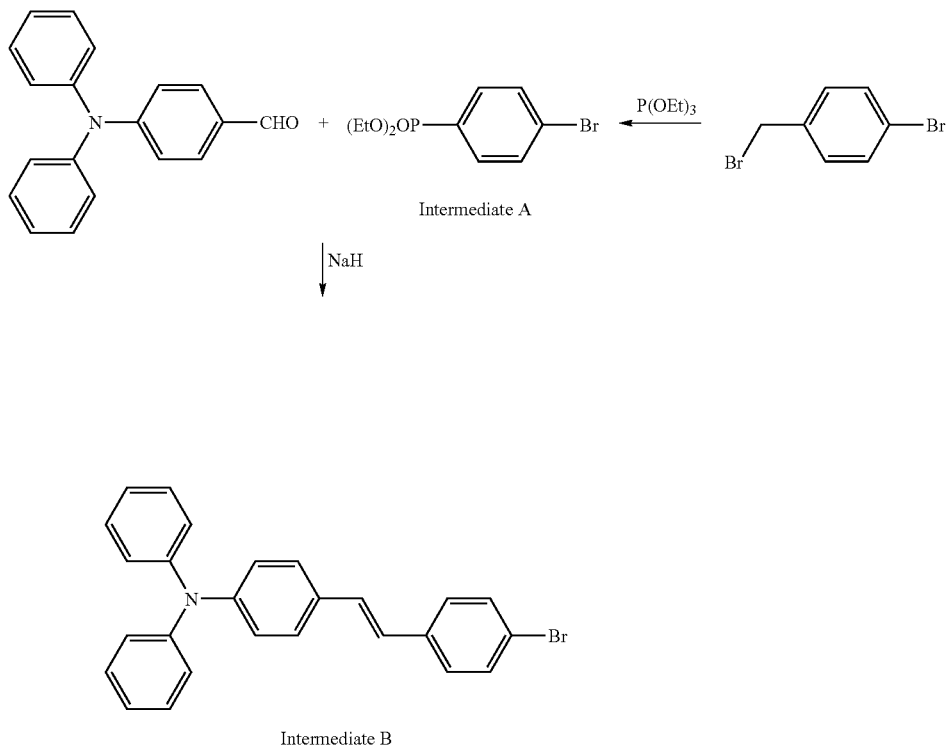

Intermediate A

Intermediate B

Synthesis Example 1

Synthesis of Intermediate A 3 g (12 mmol) of 4-bromobenzyl bromide was mixed with 4.5 g (18 mmol) of P(OCH$_2$CH$_3$)$_3$ and the mixture was stirred at 185° C. for 6 hours. The reactant was cooled to room temperature to obtain a crude product, which was then separated and purified using a silica gel column chromatography to obtain 3.13 g of Intermediate A (Yield: 85%).

Synthesis Example 2

Synthesis of Intermediate B 1.286 g (4.39 mmol) of Intermediate A was dissolved in 100 ml of a tetrahydrofurane solvent, and then 0.157 g (6.57 mmol) of sodium hydride was added thereto. The mixture was reacted at 50° C. for 1 hour. Then, 1 g (3.66 mmol) of 4-(N, N-diphenylamino)benzaldehyde was dropped to the solution and reacted at 70° C. for one day. 20 ml of ethanol was added to the resultant product and then dried in a vacuum condition, and 200 ml of methylenechloride was added thereto. The resulting organic layer was collected and twice washed using 50 ml of water. The washed organic layer was dried over anhydride magnesium sulfate, and then filtered to remove precipitates. The filtered organic layer was dried to evaporate the solvent. Then, the resultant product was separated and purified using a silica gel column chromatography to obtain 1.17 g of Intermediate B (Yield: 77%).

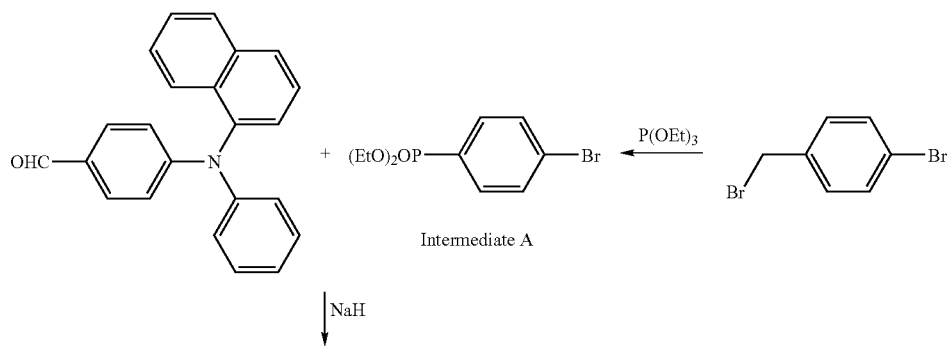

Intermediate A

-continued
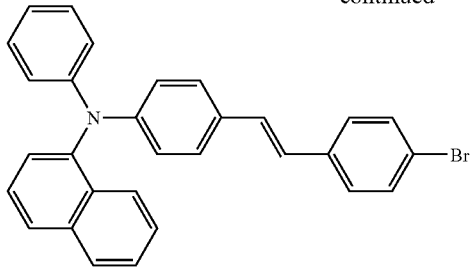
Intermediate C
Synthesis Example 3
Synthesis of Intermediate C
1.18 g of Intermediate C (Yield: 68%) was obtained in the same manner as in Synthesis Example 2, except that 4-(N,N-phenylnaphthylamino)benzaldehyde was used instead of the 4-(N,N-diphenylamino)benzaldehyde.
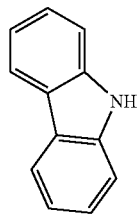
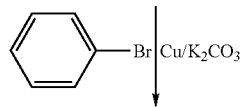
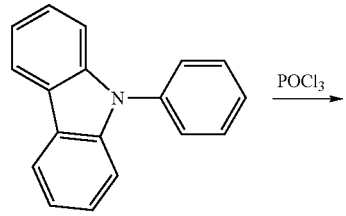
Intermediate D
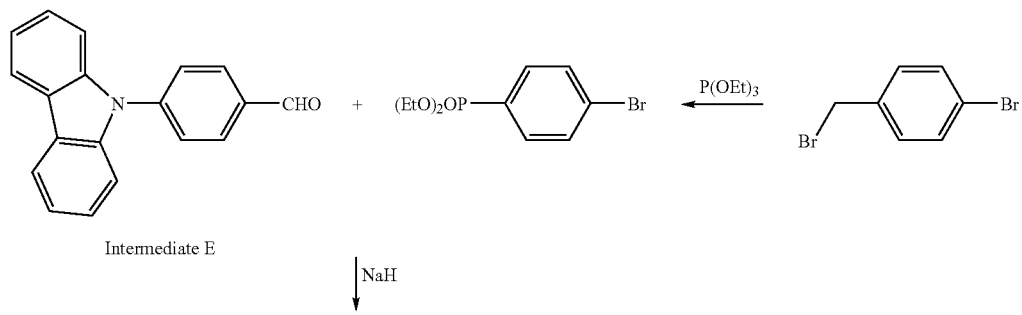
Intermediate E

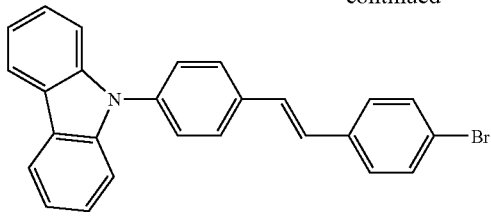

Intermediate F

Synthesis Example 4

Synthesis of Intermediate D 3 g (19.10 mmol) of bromobenzene, 0.3 g (4.60 mmol) of copper powder, 3.83 g of (22.90 mmol) of carbazole, and 4.75 g (34.35 mmol) of $K_2CO_3$ were diluted using 150 ml of ortho-dichlorobenzene and stirred at 185° C. for 48 hours. The reactant was cooled to room temperature and 100 ml of chloroform was added thereto. The resultant solution was filtered and then the organic solvent was removed under a reduced pressure to obtain a crude product. The crude product was separated and purified using a silica gel column chromatography to obtain 2.3 g of Intermediate D (Yield: 56%).

Synthesis Example 5

Synthesis of Intermediate E 7.84 g (36.6 mmol) of Intermediate D was dissolved in 100 ml of DMF, and then 5.61 g (36.6 mmol) of phosphorus oxychloride was slowly added to the mixture and stirred at 100° C. for 5 hours. The reactant was cooled to room temperature and 100 ml of dichloromethane was added thereto. The obtained organic layer was twice washed using 50 ml of water. The washed organic layer was dried over anhydride magnesium sulfate, and then filtered to remove the precipitates. The filtered organic layer was dried to evaporate the solvent. Then, the resultant product was separated and purified using a silica gel column chromatography to obtain 8.01 g of Intermediate E (Yield: 90%).

Synthesis Example 6

Synthesis of Intermediate F 0.89 g of Intermediate F (Yield: 61%) was obtained in the same manner as in Synthesis Example 2, except that Intermediate D was used instead of the 4-(N,N-diphenylamino)benzaldehyde.

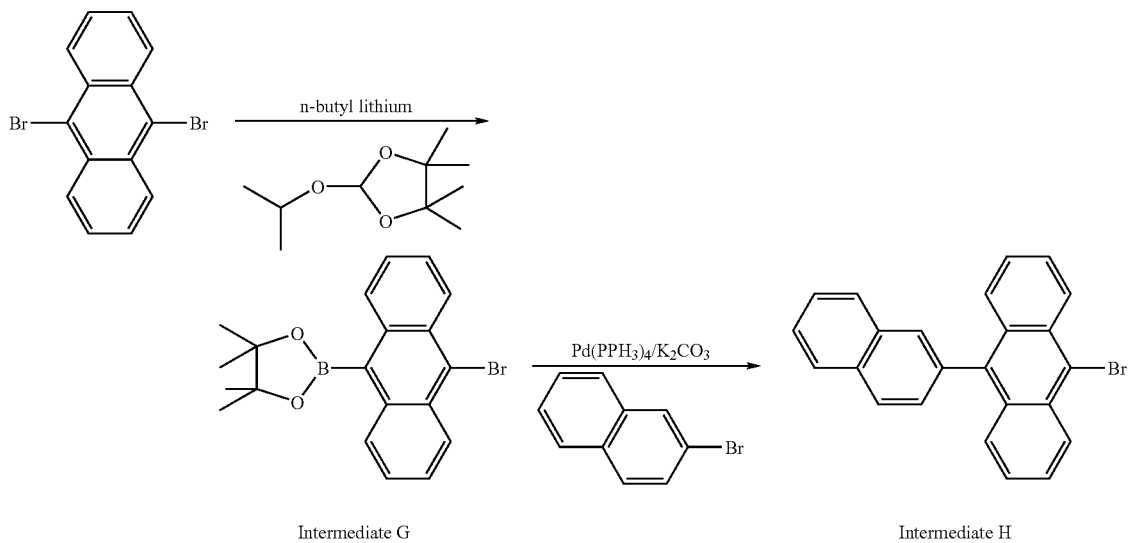

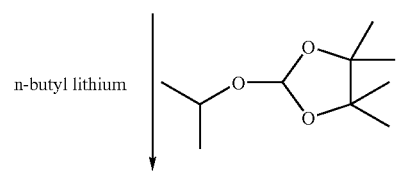

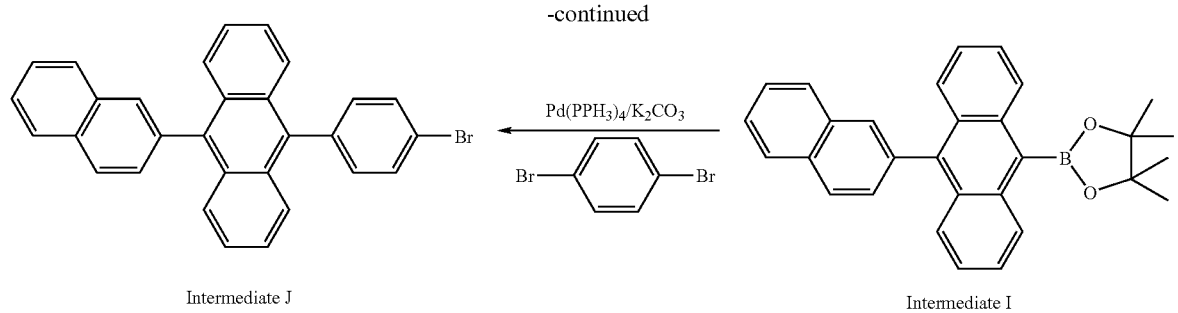

Intermediate J          Intermediate I

Synthesis Example 7

Synthesis of Intermediate G 2.36 g of (7.04 mmol) of 9,10-dibromoanthracene was dissolved in 100 ml of a tetrahydrofurane solvent, and then 4.8 ml (7.70 mmol) of 1.6M normal-butyllithium was slowly added thereto at −78° C. and reacted at −78° C. for 20 minutes. Then, 1.31 g (7.04 mmol) of 2-isopropoxy-4,4,5,5-tetramethyl-1,3,2-dioxabororane was slowly added to the reactant at −78° C. and the temperature was slowly increased to room temperature. Then, the resultant mixture was reacted at room temperature for 24 hours, 50 ml of water was added thereto, and 100 ml of diethylether was added to the water added mixture and shaken. The obtained organic layer was dried over anhydride magnesium sulfate, and then filtered to remove the used anhydride magnesium sulfate. The filtered organic layer was dried to evaporate the solvent. The resultant product was separated and purified using a silica gel column chromatography to obtain 1.94 g of Intermediate G (Yield: 72%).

Synthesis Example 8

Synthesis of Intermediate H 4.06 g of (10.6 mmol) of Intermediate G, 2.2 g of (15.9 mmol) of K₂CO₃, 2 g of (9.66 mmol) of 2-bromonaphthalene, 7.84 g of (36.6 mmol) of tetrakis(triphenylphosphine)palladium(0) were diluted in a solvent of 100 ml of tetrahydrofurane and 20 ml of water and stirred at 85° C. for 15 hours. The mixture was cooled to room temperature and 100 ml of diethylether was added thereto. The obtained organic layer was twice washed using 50 ml of water. The washed organic layer was dried over anhydride magnesium sulfate, and then filtered to remove the precipitates. The filtered organic layer was dried to evaporate the solvent. The resultant product was separated and purified using a silica gel column chromatography to obtain 2.78 g of Intermediate H (Yield: 76%).

Synthesis Example 9

Synthesis of Intermediate I 2.09 g of Intermediate I (Yield: 69%) was obtained in the same manner as in Synthesis Example 7, except that Intermediate H was used instead of the 9,10-dibromoanthracene.

Synthesis Example 10

Synthesis of Intermediate J 2.35 g of Intermediate J (Yield: 53%) was obtained in the same manner as in Synthesis Example 8, except that Intermediate I was used instead of the Intermediate G and 1,4-dibromobenzene was used instead of the 2-bromonaphthalene.

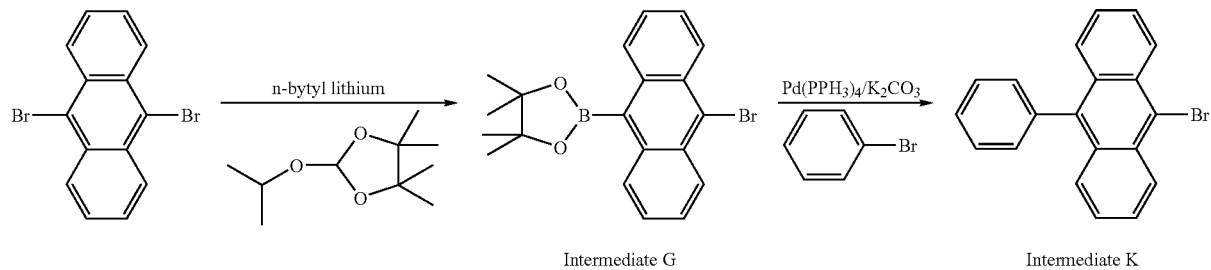

Intermediate G          Intermediate K

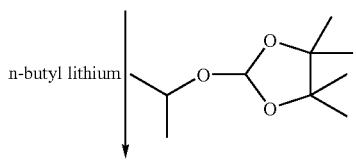

-continued

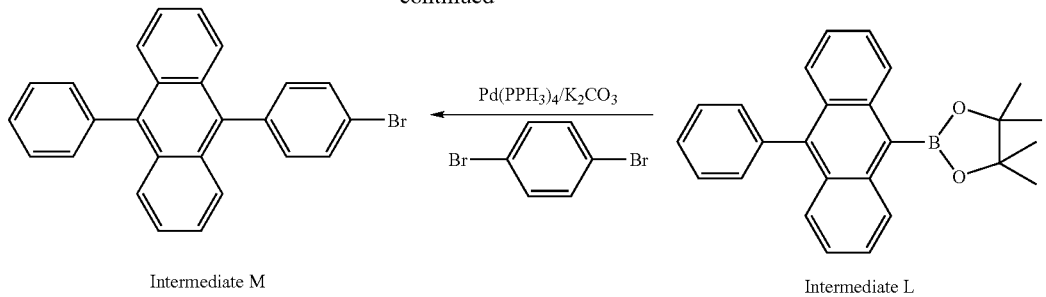

Intermediate M          Intermediate L

Synthesis Example 11

Synthesis of Intermediate K 2.51 g of Intermediate K (Yield: 78%) was obtained in the same manner as in Synthesis Example 8, except that bromobenzene was used instead of the 2-bromonaphthalene.

Synthesis Example 12

Synthesis of Intermediate L 1.95 g of Intermediate L (Yield: 73%) was obtained in the same manner as in Synthesis Example 7, except that Intermediate K was used instead of the 9,10-dibromoanthracene.

Synthesis Example 13

Synthesis of Intermediate M 2.33 g of Intermediate M (Yield: 59%) was obtained in the same manner as 4 in Synthesis Example 8, except that Intermediate L was used instead of the Intermediate G and 1,4-dibromobenzene was used instead of the 2-bromonaphthalene.

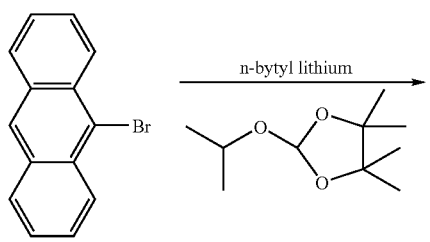

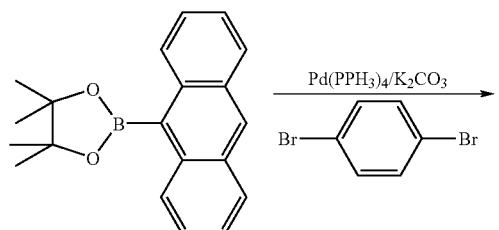

Intermediate N

-continued

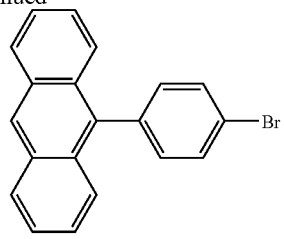

Intermediate O

Synthesis Example 14

Synthesis of Intermediate N 1.61 g of Intermediate N (Yield: 75%) was obtained in the same manner as in Synthesis Example 7, except that 9-bromoanthracene was used instead of the 9,10-dibromoanthracene.

Synthesis Example 15

Synthesis of Intermediate O 1.99 g of Intermediate O (Yield: 62%) was obtained in the same manner as in Synthesis Example 8, except that Intermediate N was used instead of the Intermediate G and 1,4-dibromobenzene was used instead of the 2-bromonaphthalene.

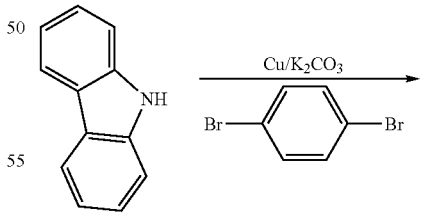

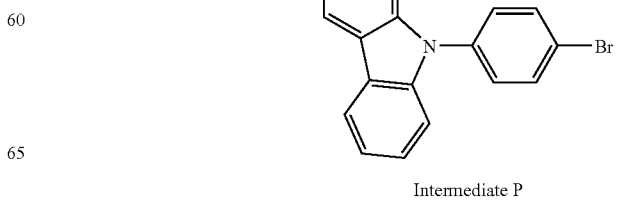

Intermediate P

Synthesis Example 16

Synthesis of Intermediate P 2.53 g of Intermediate P (Yield: 45%) was obtained in the same manner as in Synthesis Example 4, except that 1,4-dibromobenzene was used instead of bromobenzene.

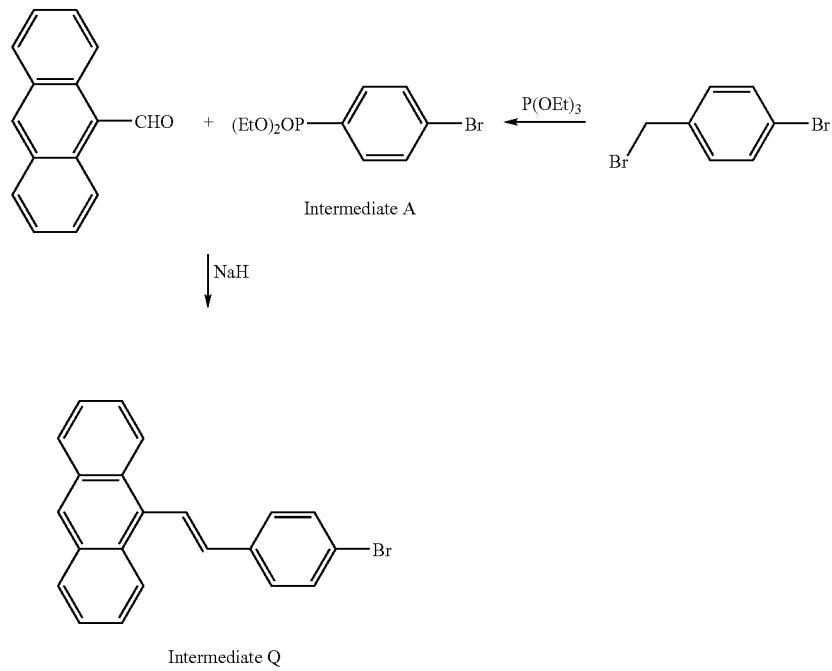

Synthesis Example 17

Synthesis of Intermediate Q 0.88 g of Intermediate Q (Yield: 67%) was obtained in the same manner as in Synthesis Example 2, except that 9-anthracenecarboxaldehyde was used instead of the 4-(N,N-diphenylamino)benzaldehyde.

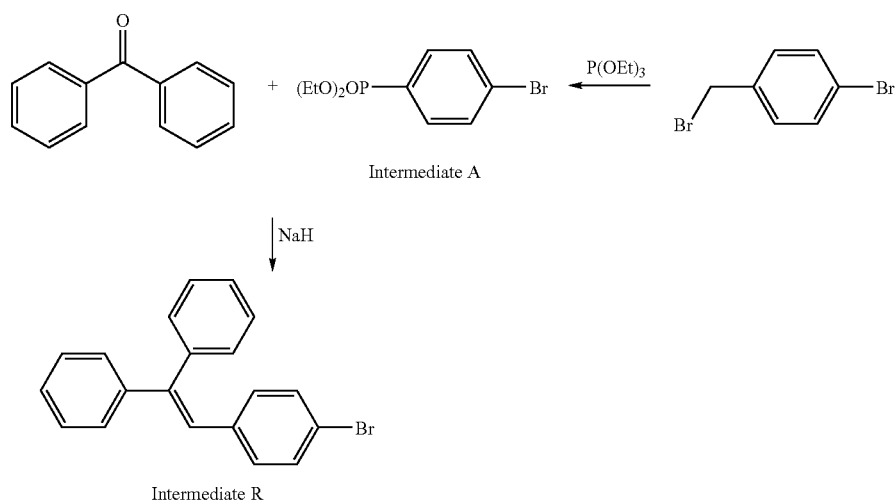

Synthesis Example 18
Synthesis of Intermediate R
0.87 g of Intermediate R (Yield: 71%) was obtained in the same manner as in Synthesis Example 2, except that benzophenone was used instead of the 4-(N,N-diphenylamino)benzaldehyde.
Example 1
Synthesis of Compound 2 Represented by Formula 2
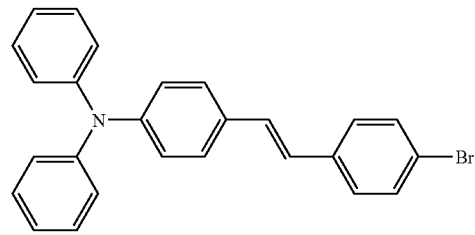
Intermediate B
| t-butyl lithium
| 1,3-dichlorotetramethyldisiloxane
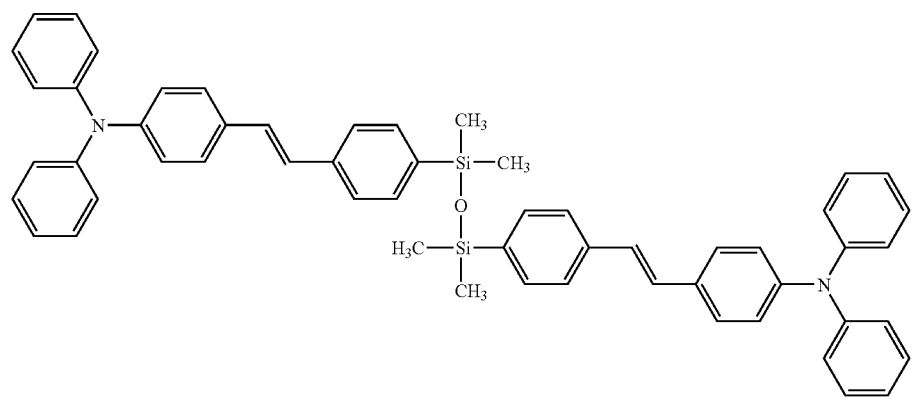

2.00 mmol of Intermediate B substituted with mono brome was dissolved in 50 ml of a tetrahydrofurane, and 2.10 mmol of tertiary-butyllithium was slowly added thereto at −78° C.

The mixture was reacted at −78° C. for one hour and 0.98 mmol of 1,3-dichlorotetramethyldisiloxane compound was slowly added thereto at −78° C. The temperature was slowly increased to room temperature. The resulting mixture was reacted at room temperature for 10 hours and 50 ml of water was added thereto. 100 ml of diethylether was added to the resulting solution and then was shaken. The obtained organic layer was dried over anhydride magnesium sulfate, and then filtered to remove the precipitates. The filtered organic layer was dried to evaporate the solvent. The resultant product was separated and purified using a silica gel column chromatography to obtain Organosiloxane Compound 2 represented by Formula 2.

Example 2

Synthesis of Compound 3 Represented by Formula 3

Organosiloxane Compound 3 represented by Formula 3 was prepared in the same manner as in Example 1, except that 1,5-dichlorohexamethyltrisiloxane was used instead of the 1,3-dichlorotetramethylsiloxane.

Example 3

Synthesis of Compound 4 Represented by Formula 4

Organosiloxane Compound 4 represented by Formula 4 was prepared in the same manner as in Example 1, except that 1,7-dichlorooctamethyltetrasiloxane was used instead of 1,3-dichlorotetramethylsiloxane.

Example 4

Synthesis of Compound 5 Represented by Formula 5

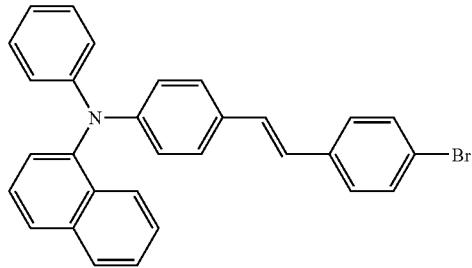

intermediate C t-butyl lithium
1, 3-dichlorotetramethyldisiloxane

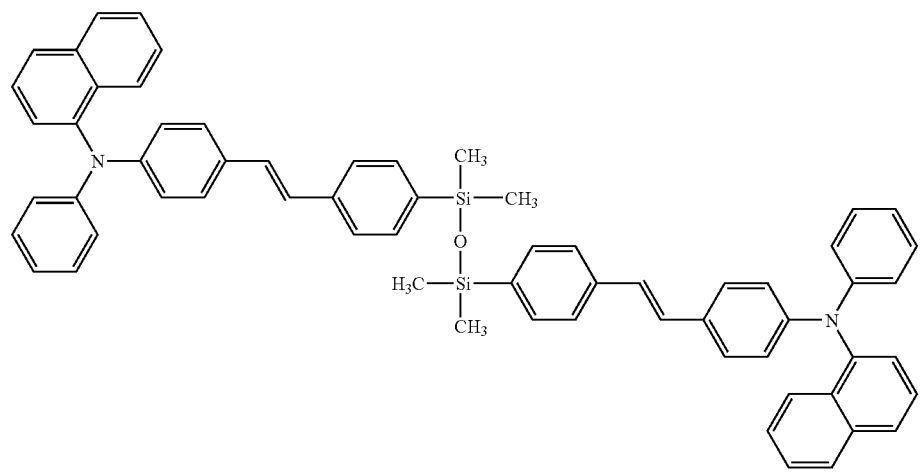

Organosiloxane Compound 5 represented by Formula 5 was prepared in the same manner as in Example 1, except that Intermediate C was used instead of the Intermediate A.
Example 5
Synthesis of Compound 6 Represented by Formula 6
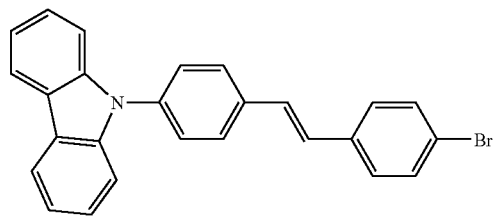
intermediate F
↓ t-butyl lithium
1, 3-dichlorotetramethyldisiloxane
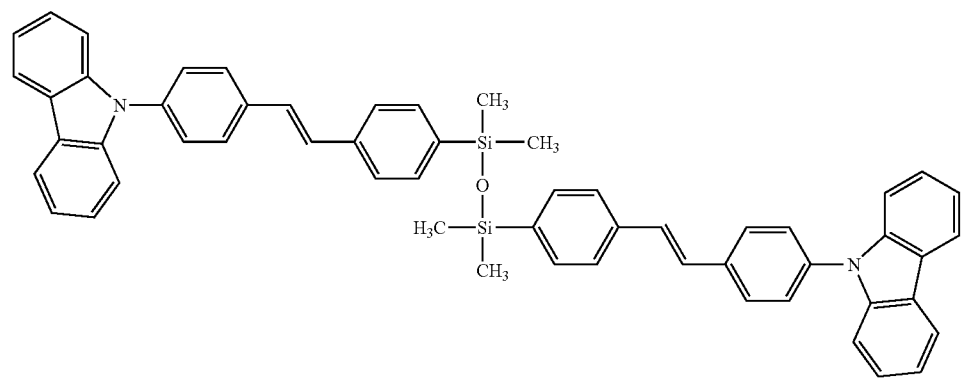

Organosiloxane Compound 6 represented by Formula 6 was prepared in the same manner as in Example 1, except that Intermediate F was used instead of Intermediate A.

Example 6

Synthesis of Compound 7 Represented by Formula 7

Organosiloxane Compound 7 represented by Formula 7 was prepared in the same manner as in Example 1, except that Intermediate J was used instead of Intermediate A.

Example 7

Synthesis of Compound 8 Represented by Formula 8

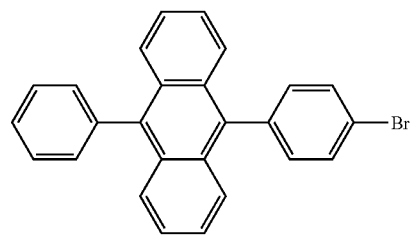

intermediate M

| t-butyl lithium
| 1, 3-dichlorotetramethyldisiloxane

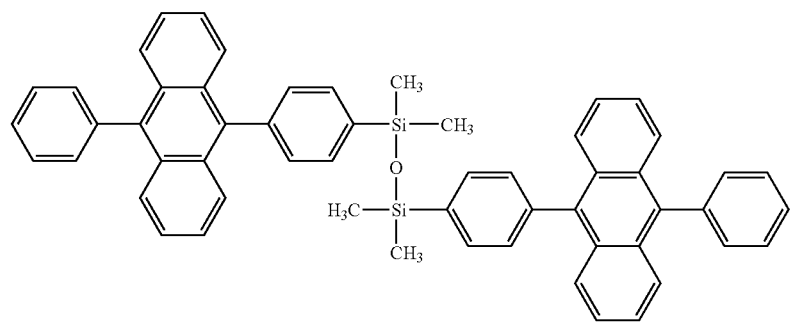

Organosiloxane Compound 8 represented by Formula 8 was prepared in the same manner as in Example 1, except that Intermediate M was used instead of Intermediate A.

Example 8

Synthesis of Compound 9 Represented by Formula 9

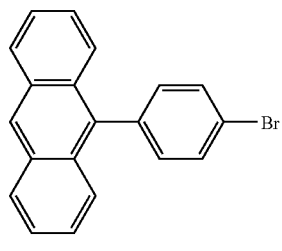

intermediate O

↓ t-butyl lithium
1, 3-dichlorotetramethyldisiloxane

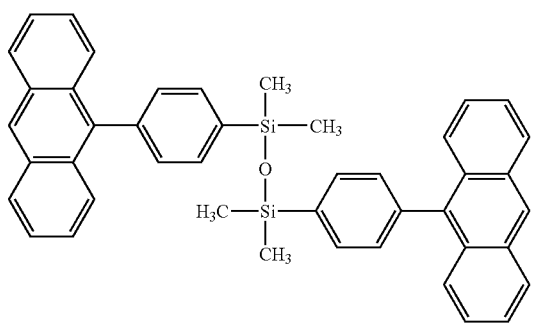

Organosiloxane Compound 9 represented by Formula 9 was prepared in the same manner as in Example 1, except that Intermediate O was used instead of Intermediate A.

Example 9

Synthesis of Compound 10 Represented by Formula 10

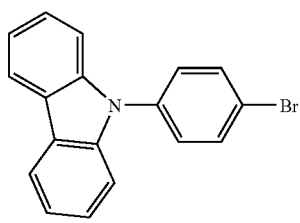

intermediate P

↓ t-butyl lithium
1, 3-dichlorotetramethyldisiloxane

-continued

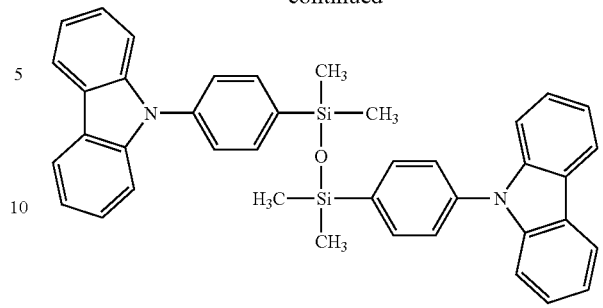

Organosiloxane Compound 10 represented by Formula 10 was prepared in the same manner as in Example 1, except that Intermediate P was used instead of Intermediate A.

Example 10

Synthesis of Compound 11 Represented by Formula 11

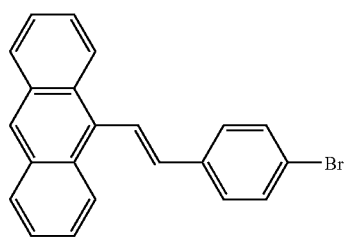

intermediate R

↓ t-butyl lithium
1, 3-dichlorotetramethyldisiloxane

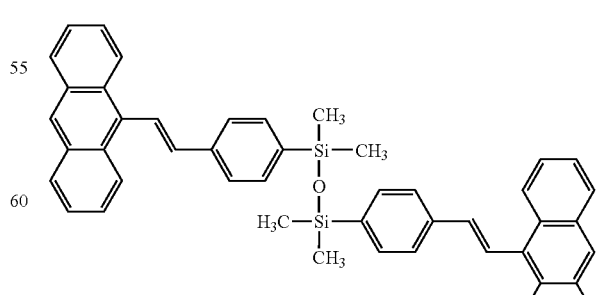

Organosiloxane Compound 11 represented by Formula 11 was prepared in the same manner as in Example 1, except that Intermediate Q was used instead of Intermediate A.

Example 11

Synthesis of Compound 12 Represented by Formula 12

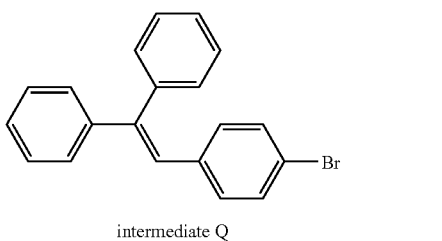

intermediate Q t-butyl lithium
1, 3-dichlorotetramethyldisiloxane

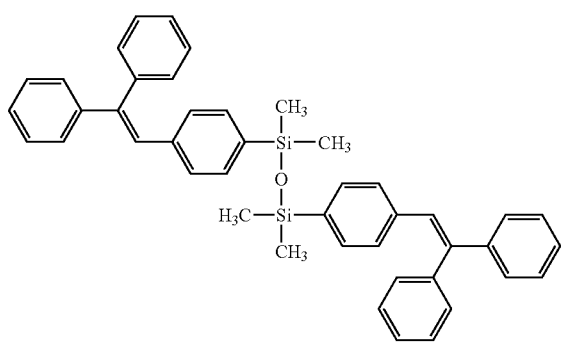

Organosiloxane Compound 12 represented by Formula 12 was prepared in the same manner as in Example 1, except that Intermediate R was used instead of Intermediate A.

Comparative Example 1

1 g (4.39 mmol) of benzylphosphonic acid diethylester was dissolved in 100 ml of tetrahydrofurane solvent, and then 0.157 g (6.57 mmol) of sodium hydride was added thereto. The mixture was reacted at 50° C. for one hour. 1 g of 4-(N,N-diphenylamino)benzaldehyde (3.66 mmol) was dropped to the reactant and reacted at 70° C. for one day. 20 ml of ethanol was added to the resulting reactant, dried in a vacuum condition, and 200 ml of methylenechloride was added thereto. The obtained organic layer was twice washed using 50 ml of water. The washed organic layer was dried over anhydride magnesium sulfate, and then filtered to remove the precipitates. The filtered organic layer was dried to evaporate the solvent. Then, the resultant product was separated and purified using a silica gel column chromatography to obtain Comparative Compound A represented by Formula A having an yield of 78%.

<Formula A>

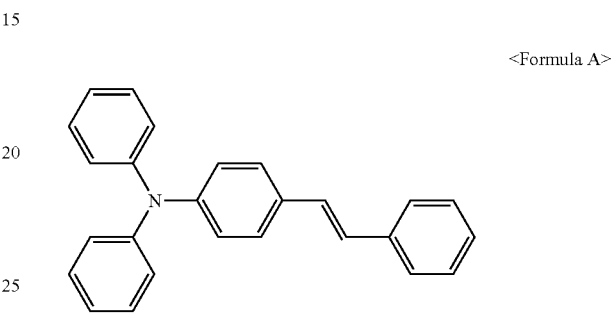

Comparative Example 2

0.824 g (2.00 mmol) of Intermediate B was dissolved in 50 ml of tetrahydrofurane, and then 1.23 ml (2.10 mmol) of 1.7M tertiary-butyllithium was slowly added thereto at −78° C.

The mixture was reacted at −78° C. for one hour and 0.98 mmol of dichlorodiphenylsilane was slowly added thereto at −78° C. The temperature was slowly increased to room temperature. The resulting mixture was reacted at room temperature for 10 hours and 50 ml of water was added thereto. 100 ml of diethylether was added to the resulting solution and then was shaken. The resulting organic layer was separated and dried over anhydride magnesium sulfate, and then filtered to remove the precipitates. The filtered organic layer was dried to evaporate the solvent. The resultant product was separated and purified using a silica gel column chromatography to obtain 0.53 g of Comparative Compound A (Yield: 64%) represented by Formula B.

<Formula B>

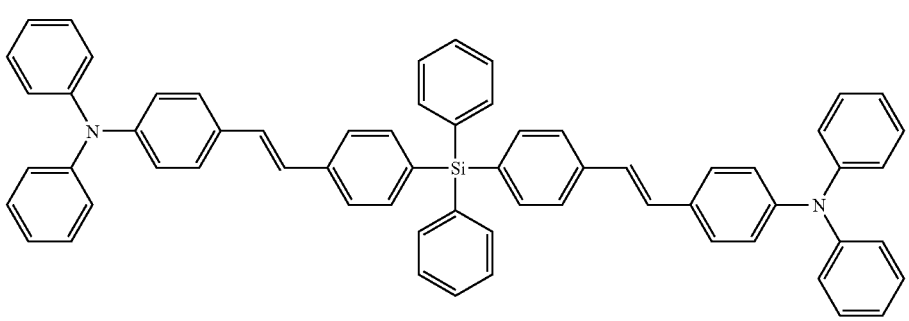

Measurement Example 1

Luminous Properties of Comparative Compounds A and B and Compounds 2 Through 12

Absorption spectra and photoluminescence (PL) spectra of Comparative Compounds A and B and Compounds 2 through 12 were measured to determine luminous properties of respective compounds. First, Compound 2 was diluted using toluene to have a concentration of 0.2 mM, and an absorption spectrum of Compound 2 was measured using a Shimadzu UV-350 spectrometer. The same experiment was performed on Compounds 3 through 12 and Comparative Compounds A and B. Meanwhile, Compound 2 was diluted using toluene to have a concentration of 10 mM, and a PL spectrum of Compound 2 was measured using an ISC PC1 spectrofluorometer including a Xenon lamp. The same experiment was performed on Compounds 3 through 12 and Comparative Compounds A and B.

The results are shown in Table 1:

TABLE 1

| Compound No | Maximum Absorption Wavelength (nm) | Minimum PL Wavelength(nm) |
|---|---|---|
| A | 368 | 423 |
| B | 370 | 428 |
| 2 | 378 | 446 |
| 3 | 378 | 446 |
| 4 | 378 | 448 |
| 5 | 378 | 438 |
| 6 | 376 | 436 |
| 7 | 360, 381, 396 | 430 |
| 8 | 358, 376, 389 | 425 |
| 9 | 358, 376, 389 | 423 |
| 10 | 375 | 441 |
| 11 | 360, 382, 401 | 438 |
| 12 | 371 | 435 |

Measurement Example 2

Device Characteristics of Comparative Samples A and B and Compounds 2 Through 12

An organic light-emitting device was manufactured using Comparative Compound A as a dopant of an emitting layer. The structure of the organic light-emitting device is ITO/PEDOT(500 Å)/Comparative Compound A_PVK (480 Å)TAZ(200 Å)/LiF(10 Å)/Al(2000 Å).

In order to prepare an anode, ITO glass substrate 15 Ω/cm² (1200 Å) produced by Corning Inc. was cut to a size of 50 mm×50 mm×0.7 mm, sonicated using isopropyl alcohol for 5 minutes, sonicated using pure water for 5 minutes, and washed using ultra violet (UV) ozone for 30 minutes. Then, PEDOT-PSS (AI4083) produced by Bayer Inc. was coated on the prepared anode and heat treated at 120° C. for 5 hours to form a HIL having a thickness of 500 Å. A mixture of 0.1 g of PVK and 0.01 g of Comparative Compound A (10 parts by weight of Comparative Compound A based on 100 parts by weight of PVK) was spin coated on the HIL and then heat treated at 110° C. for 2 hours to form an EML having a thickness of 480 Å. Then, a TAZ compound was spin coated on the EML and then heat treated at 110° C. for 2 hours to form an ETL having a thickness of 200 Å. LiF was vacuum deposited on the ETL to form an EIL having a thickness of 10 Å and then Al was vacuum deposited on the EIL to form a cathode having a thickness of 2000 Å. As a result, an organic light-emitting device illustrated in FIG. 1A was completely manufactured. The obtained organic light-emitting device will be referred to as Comparative Sample A.

Organic light-emitting devices were manufactured in the same manner as in Comparative Sample A, except that emitting layers were formed using Comparative Compound B, and Compounds 2 through 12 respectively prepared according to Comparative Example 2, and Synthesis Examples 2 through 12, respectively. The obtained respective organic light-emitting devices will be referred to as Comparative Sample B, and Samples 2 through 12.

Operating voltages, Color purities, and Efficiencies of Comparative Sample A, B, and Samples 2 through 12 were measured using a PR650 (Spectroscan) Source Measurement Unit. The results are shown in Table 2.

TABLE 2

| Sample No | Operating Voltage (V) | CIE Color Coordinate (~100 cd/m2) | Efficiency at 7.2 V (cd/A) |
|---|---|---|---|
| A | 4.7 | (0.16, 0.09) | 0.65 (at 10 V) |
| B | 4.6 | (0.16, 0.09) | 0.65 (at 8 V) |
| 2 | 4.2 | (0.15, 0.08) | 1.64 (at 7 V) |
| 3 | 4.4 | (0.16, 0.09) | 1.55 (at 8 V) |
| 4 | 4.4 | (0.16, 0.09) | 1.53 (at 8 V) |
| 5 | 4.2 | (0.16, 0.09) | 1.76 (at 7 V) |
| 6 | 4.5 | (0.15, 0.09) | 1.20 (at 8 V) |
| 7 | 4.7 | (0.13, 0.09) | 1.13 (at 9 V) |
| 8 | 4.6 | (0.13, 0.08) | 1.03 (at 9 V) |
| 9 | 4.6 | (0.14, 0.09) | 1.00 (at 10 V) |
| 10 | 4.7 | (0.15, 0.09) | 1.10 (at 10 V) |
| 11 | 4.5 | (0.15, 0.09) | 1.27 (at 10 V) |
| 12 | 4.5 | (0.15, 0.08) | 1.35 (at 10 V) |

As shown in Table 2, Samples 2 through 10 exhibited better properties than Comparative Samples A and B.

An organosiloxane compound represented by Formula 1 according to the present invention can be used to form a thin film having good film properties. Accordingly, an organic light-emitting device using the organosiloxane compound has a low operating voltage, high color purity, and high efficiency.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An organosiloxane compound represented by Formula 1:

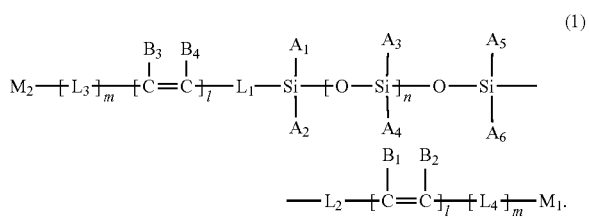

where $L_1$, $L_2$, $L_3$, and $L_4$ are each independently a substituted or unsubstituted $C_6$-$C_{30}$ arylene group, or a substituted or unsubstituted $C_2$-$C_{30}$ heteroarylene group;

$M_1$ and $M_2$ are each independently

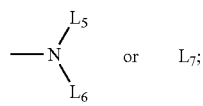

$L_5$, $L_6$, and $L_7$ are each independently a substituted or unsubstituted $C_6$-$C_{30}$ aryl group, or a substituted or unsubstituted $C_2$-$C_{30}$ heteroaryl group, and $L_5$ and $L_6$ are optionally connected to form a substituted or unsubstituted ring having the N atom;

$A_1$, $A_2$, $A_3$, $A_4$, $A_5$, and $A_6$ are each independently hydrogen, a substituted or unsubstituted $C_1$-$C_{20}$ alkyl group, or a substituted or unsubstituted $C_6$-$C_{30}$ aryl group;

$B_1$, $B_2$, $B_3$, and $B_4$ are each independently hydrogen, a substituted or unsubstituted $C_1$-$C_{20}$ alkyl group, or a substituted or unsubstituted $C_6$-$C_{30}$ aryl group;

n is an integer of 0 through 5;

l is an integer of 1; and m is an integer of 0 through 3.

2. The organosiloxane compound of claim 1, wherein $L_1$, $L_2$, $L_3$, and $L_4$ are each independently a substituted or unsubstituted phenylene group, a substituted or unsubstituted naphthylene group, a substituted or unsubstituted anthracenylene group, a substituted or unsubstituted phenanthrylene group, a substituted or unsubstituted fluorenylene group, a substituted or unsubstituted carbazoylene group, a substituted or unsubstituted thiophenylene group, a substituted or unsubstituted thiazolylene group;

$M_1$ and $M_2$ are each independently

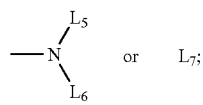

$L_5$, $L_6$, and $L_7$ are each independently a substituted or unsubstituted phenyl group, a substituted or unsubstituted naphthyl group, a substituted or unsubstituted anthracenyl group, a substituted or unsubstituted phenanthrenyl group; and $L_5$, and $L_6$ can be connected to form a substituted or unsubstituted ring containing the N atom.

3. The organosiloxane compound of claim 1, wherein a substituent of the alkyl group, the aryl group, the heteroaryl group, and the cycloalkyl group comprises at least one material selected from the group consisting of —F; —Cl; —Br; —CN; —NO₂; —OH; an unsubstituted $C_1$-$C_{20}$ alkyl group; a $C_1$-$C_{20}$ alkyl group substituted with —F, —Cl, —Br, —CN, —NO₂, or —OH; an unsubstituted $C_1$-$C_{20}$ alkoxy group; a $C_1$-$C_{20}$ alkoxy group substituted with —F, —Cl, —Br, —CN, —NO₂, or —OH; an unsubstituted $C_6$-$C_{30}$ aryl group; a $C_6$-$C_{30}$ aryl group substituted with —F, —Cl, —Br, —CN, —NO₂, or —OH; an unsubstituted $C_2$-$C_{30}$ heteroaryl group; a $C_2$-$C_{30}$ heteroaryl group substituted with —F, —Cl, —Br, —CN, —NO₂, or —OH; an unsubstituted $C_5$-$C_{20}$ cycloalkyl group; and a $C_5$-$C_{20}$ cycloalkyl group substituted with —F, —Cl, —Br, —CN, —NO₂, or —OH.

4. The organosiloxane compound of claim 1, wherein $L_1$, $L_2$, $L_3$, and $L_4$ are each independently a phenylene group, a ($C_1$-$C_{10}$ alkyl)phenylene group, a ($C_1$-$C_{10}$ alkoxy)phenylene group, a halophenylene group, a cyanophenylene group, a dicyanophenylene group, a trifluoromethoxyphenylene group, an o-, m-, or p-tolylene group, an o-, m-, or p-cumenylene group, a mesitylene group, a phenoxyphenylene group, an (α,α-dimethylbenzene)phenylene group, a (N,N'-dimethyl)aminophenylene group, a (N,N'-diphenyl)aminophenylene group, a (($C_1$-$C_{10}$ alkyl)cyclohexyl)phenylene group, an (anthracenyl)phenylene group, a biphenylene group, a ($C_1$-$C_{10}$ alkyl)biphenylene group, a ($C_1$-$C_{10}$ alkoxy) biphenylene group, a pentalenyl group, an indenylene group, a naphthylene group, a ($C_1$-$C_{10}$ alkyl naphthylene group, a ($C_1$-$C_{10}$ alkoxy)naphthylene group, a halonaphthylene group, a cyanonaphthylene group, a biphenylenylene group, a ($C_1$-$C_{10}$ alkyl)biphenylene group, a ($C_1$-$C_{10}$ alkoxy)biphenylene group, an anthracenylene group, an azulenylene group, a heptarenylene group, an acenaphthylenylene group, a phenalenylene group, a fluorenylene group, an anthraquinolylene group, a methylanthrylene group, a phenanthrenylene group, a triphenylenylene group, a pyrenylene group, a chrysenylene group, an ethyl-chrysenylene group, a picenylene group, a perylenylene group, a chloroperylenylene group, a pentaphenylene group, a pentacenylene group, a tetraphenylenylene group, a hexaphenylene group, a hexacenylene group, a rubicenylene group, a coronenylene group, a trinaphthylenylene group, a heptaphenylene group, a heptacenylene group, a pyranthrenylene group, an ovalenylene group, a carbazolylene group, a ($C_1$-$C_{10}$ alkyl)carbazolylene group, a thio phenylene group, an indolylene group, a purinylene group, a benzimidazolylene group, a quinolinylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridinylene group, a pyridazinylene group, a pyrimidinylene group, a pyrazinylene group, a thianthrenylene group, a pyrrolidinylene group, a pyrazolidinylene group, an imidazolidinylene group, a piperidinylene group, a piperazinylene group, or a morpholynylene group.

5. The organosiloxane compound of claim 1, wherein $L_5$, $L_6$, and $L_7$ are each independently a phenyl group, a ($C_1$-$C_{10}$ alkyl)phenyl group, a ($C_1$-$C_{10}$ alkoxy)phenyl group, a halophenyl group, a cyanophenyl group, a dicyanophenyl group, a trifluoromethoxyphenyl group, an o-, m-, or p-tolyl group, an o-, m-, or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a (($C_1$-$C_{10}$ alkyl)cyclohexyl)phenyl group, an (anthracenyl)phenyl group, a ($C_1$-$C_{10}$ alkyl)biphenyl group, a ($C_1$-$C_{10}$ alkoxy)biphenyl group, a pentalenyl group, an indenyl group, a naphthyl group, a ($C_1$-$C_{10}$ alkyl) naphthyl group, a ($C_1$-$C_{10}$ alkoxy)naphthyl group, a halonaphthyl group, a cyanonaphthyl group, a biphenylenyl group, a ($C_1$-$C_{10}$ alkyl)biphenyl group, a ($C_1$-$C_{10}$ alkoxy) biphenyl group, an anthracenyl group, an azulenyl group, a heptarenyl group, an acenaphthylenyl group, a phenalenyl group, a fluorenyl group, an anthraquinolyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a ($C_{1-10}$ alkyl)carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a pyrrolidinyl group, a pyrazolidinyl group, an imidazolidinyl group, a piperidinyl group, a piperazinyl group, a carbazolyl group, a bezoxazolyl group, a phenothiazinyl group, a 5H-dibenzazepinyl group, a 5H-tribenzazepinyl group, or a morpholynyl group.

6. The organosiloxane compound of claim 1, wherein $A_1$, $A_2$, $A_3$, $A_4$, $A_5$, and $A_6$ are each independently hydrogen, methyl, ethyl, propyl, butyl, methoxy, ethoxy, a propoxy group, a butoxy group, a phenyl group, a ($C_1$-$C_{10}$ alkyl)phenyl group, a ($C_1$-$C_{10}$ alkoxy)phenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a (($C_1$-$C_{10}$ alkyl)cyclohexyl)phenyl group, an (anthracenyl)phenyl group, a biphenyl group, a ($C_1$-$C_{10}$ alkyl)biphenyl group, a ($C_1$-$C_{10}$ alkoxy)biphenyl group, a pentalenyl group, an indenyl group, a naphthyl group, a ($C_1$-$C_{10}$ alkyl) naphthyl group, a ($C_1$-$C_{10}$ alkoxy)naphthyl group, a halonaphthyl group, a cyanonaphthyl group, a biphenylenyl group, a ($C_1$-$C_{10}$ alkyl)biphenyl, a ($C_1$-$C_{10}$ alkoxy)biphenyl group, an anthracenyl group, an azulenyl group, a heptarenyl group, an acenaphthylenyl group, a phenalenyl group, a fluorenyl group, an anthraquinolyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, tetraphenylenyl group, hexaphenyl group, hexacenyl group, rubicenyl group, a coronenyl group, a trinaphthylenyl group, a heptaphenyl group, a heptacenyl group, a pyranthrenyl group, an ovalenyl group, a carbazolyl group, a cyclopentyl group, a cyclohexyl group, a ($C_1$-$C_{10}$ alkyl)cyclohexyl group, or a ($C_1$-$C_{10}$ alkoxy)cyclohexyl group.

7. The organosiloxane compound of claim 1, wherein $B_1$, $B_2$, $B_3$, and $B_4$ are each independently hydrogen, methyl, ethyl, propyl, butyl, a phenyl group, a ($C_1$-$C_{10}$ alkyl)phenyl group, a ($C_1$-$C_{10}$ alkoxy)phenyl group, a halophenyl group, a cyanophenyl group, a dicyanophenyl group, a trifluoromethoxyphenyl group, an o-, m-, or p-tolyl group, an o-, m-, or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a (($C_1$-$C_{10}$ alkyl)cyclohexyl)phenyl group, an (anthracenyl)phenyl group, biphenyl group, a ($C_1$-$C_{10}$ alkyl)biphenyl group, a ($C_1$-$C_{10}$ alkoxy)biphenyl group, a pentalenyl group, an indenyl group, a naphthyl group, a ($C_1$-$C_{10}$ alkyl) naphthyl group, a ($C_1$-$C_{10}$ alkoxy)naphthyl group, a halonaphthyl group, a cyanonaphthyl group, a biphenylenyl group, a ($C_1$-$C_{10}$ alkyl)biphenyl group, a ($C_1$-$C_{10}$ alkoxy) biphenyl group, an anthracenyl group, an azulenyl group, a heptarenyl group, an acenaphthylenyl group, a phenalenyl group, a fluorenyl group, an anthraquinolyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a cyclopentyl group, a cyclohexyl group, a ($C_1$-$C_{10}$ alkyl)cyclohexyl group, or a ($C_1$-$C_{10}$ alkoxy)cyclohexyl group.

8. The organosiloxane compound of claim 1, being represented by one of the following Formulae:

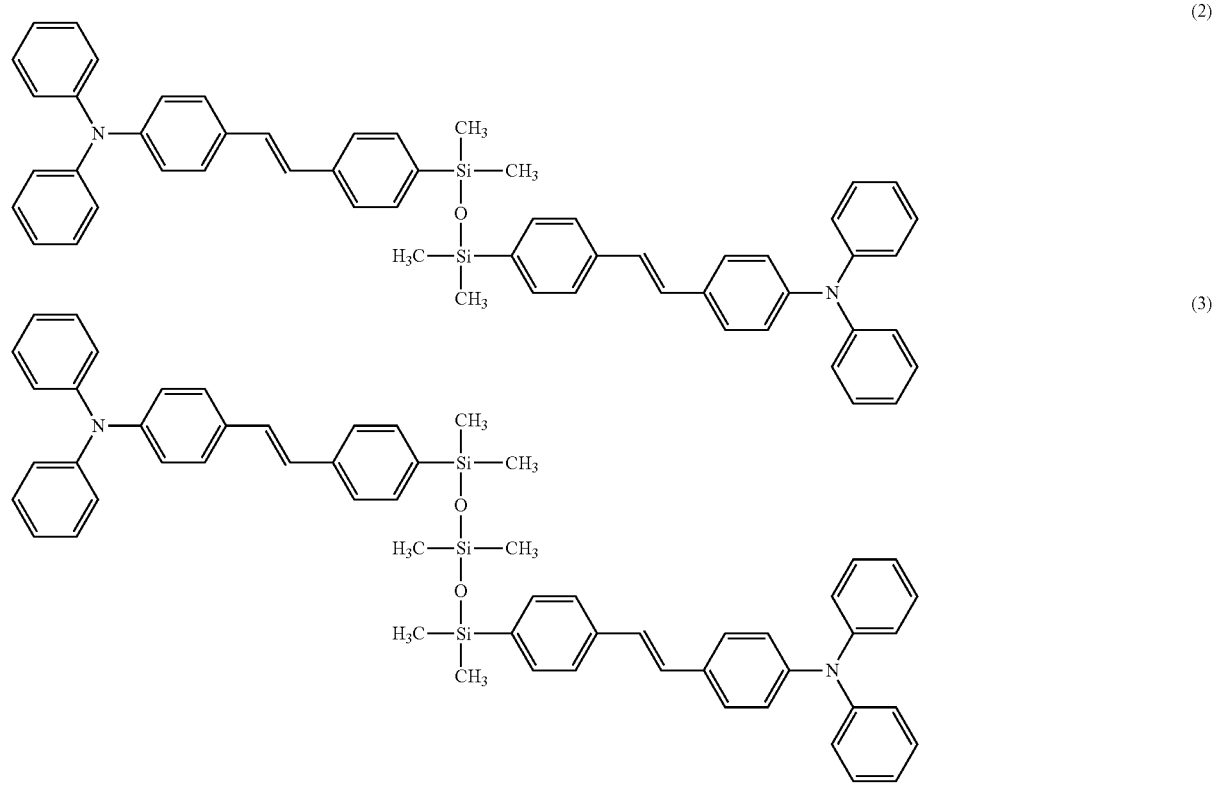

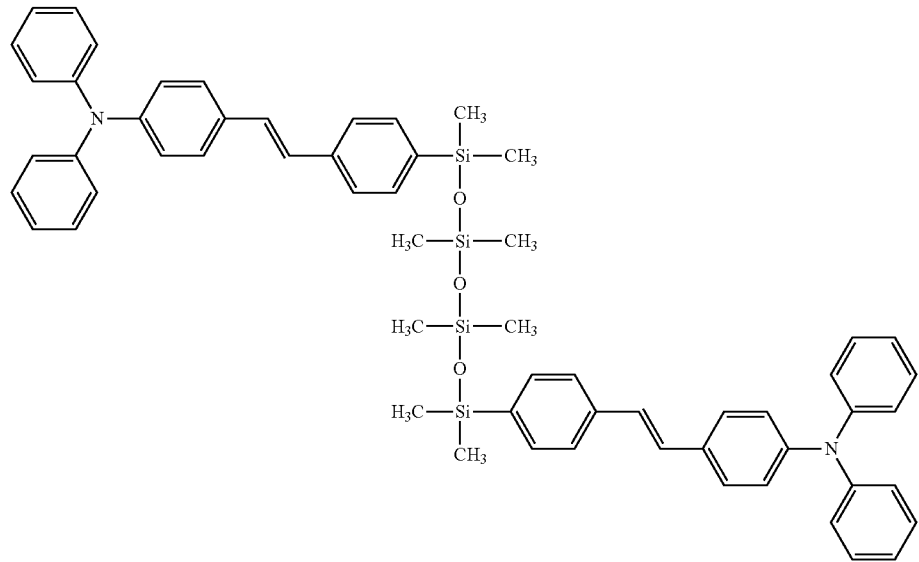
(4)
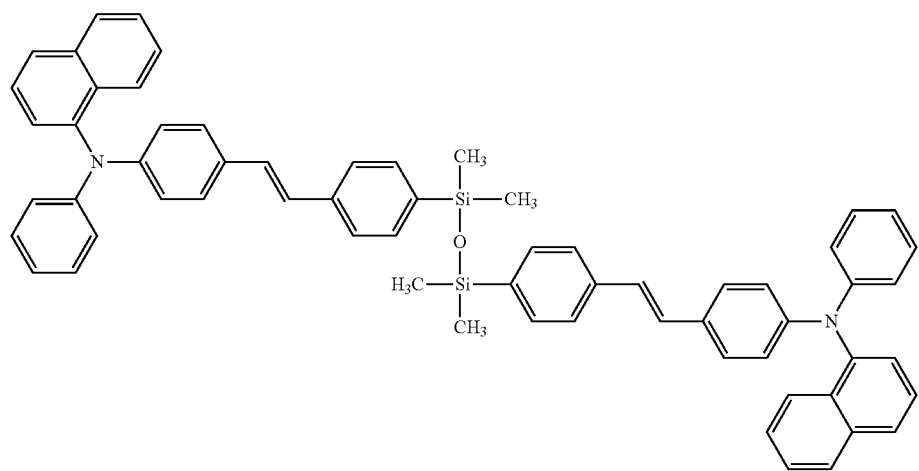
(5)
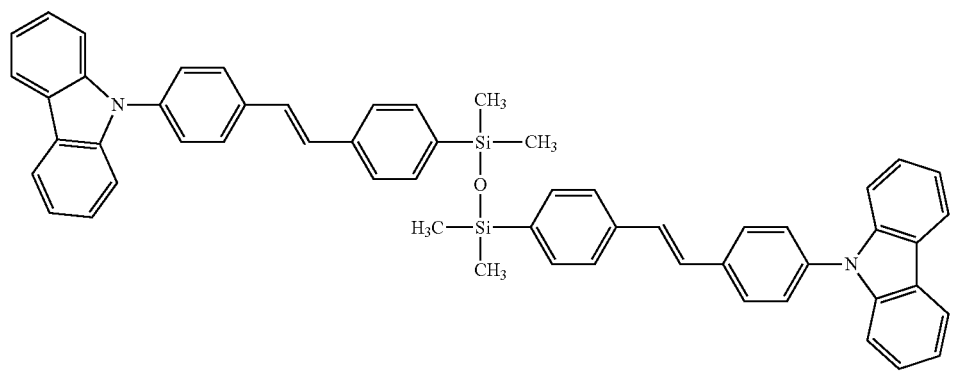
(6)

(11)
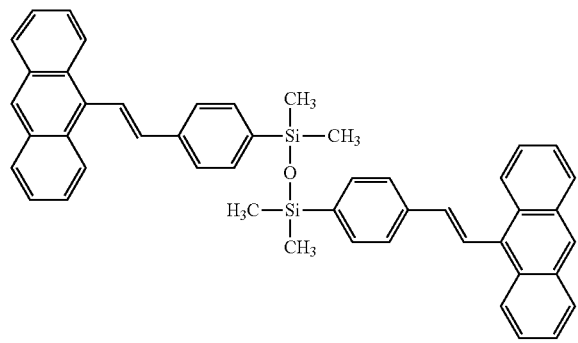
(12)
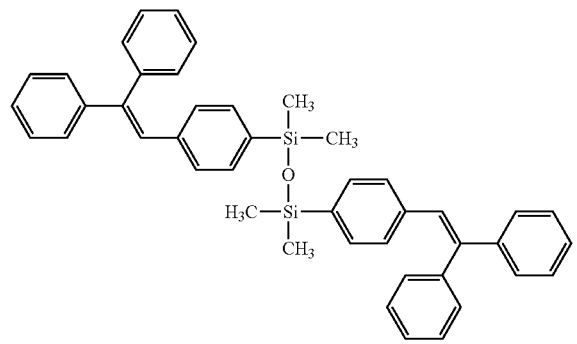
(11)
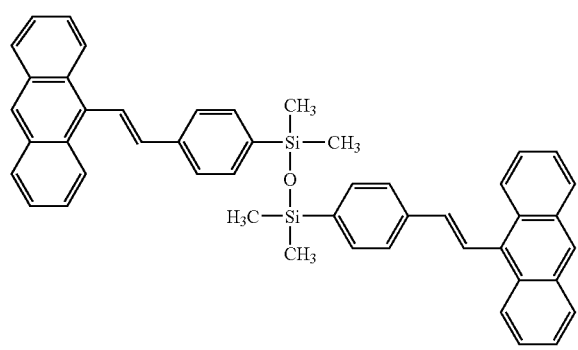
(12)
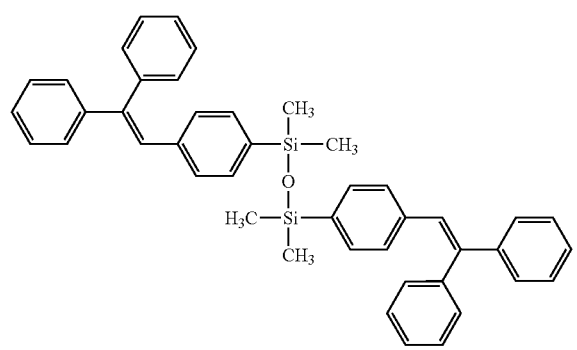
(14)
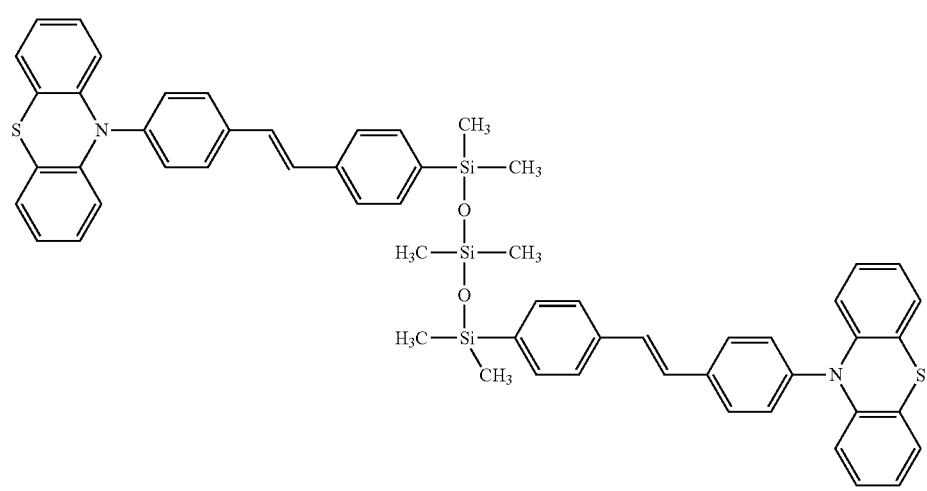

(15)
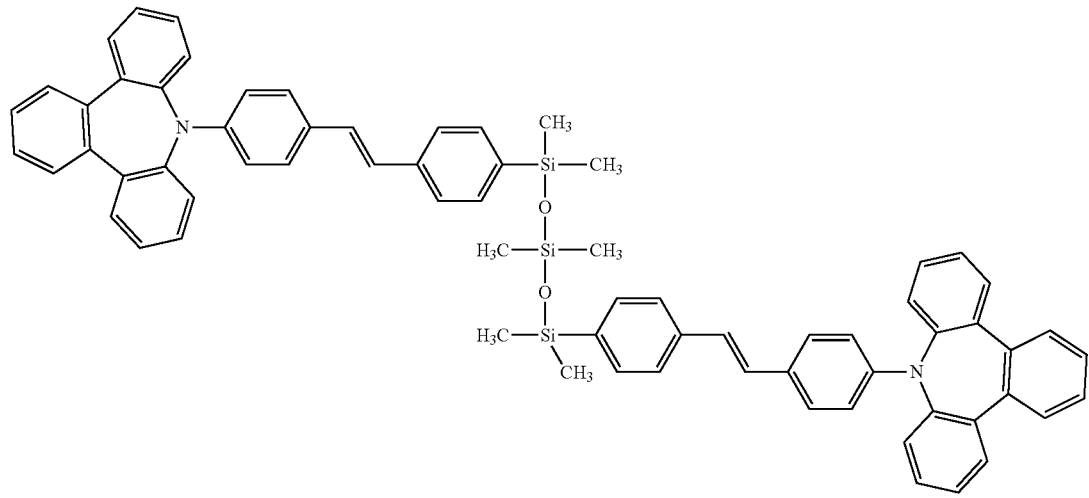
(16)
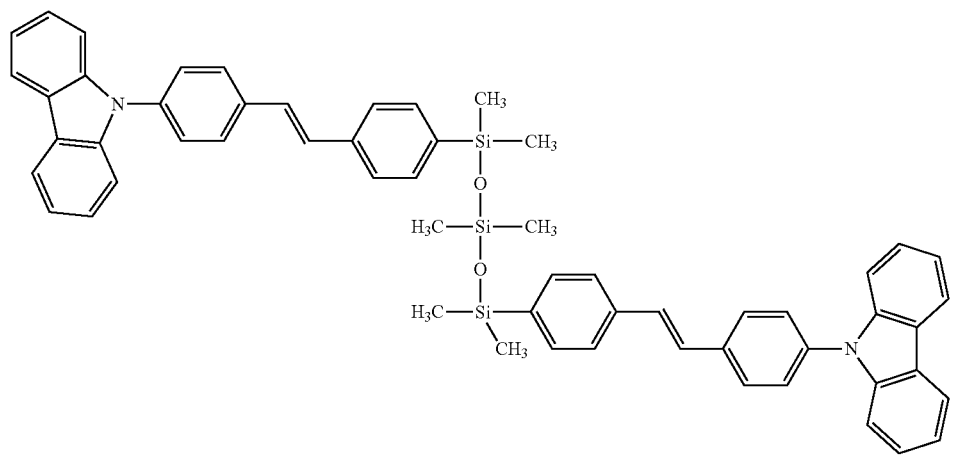
(17)
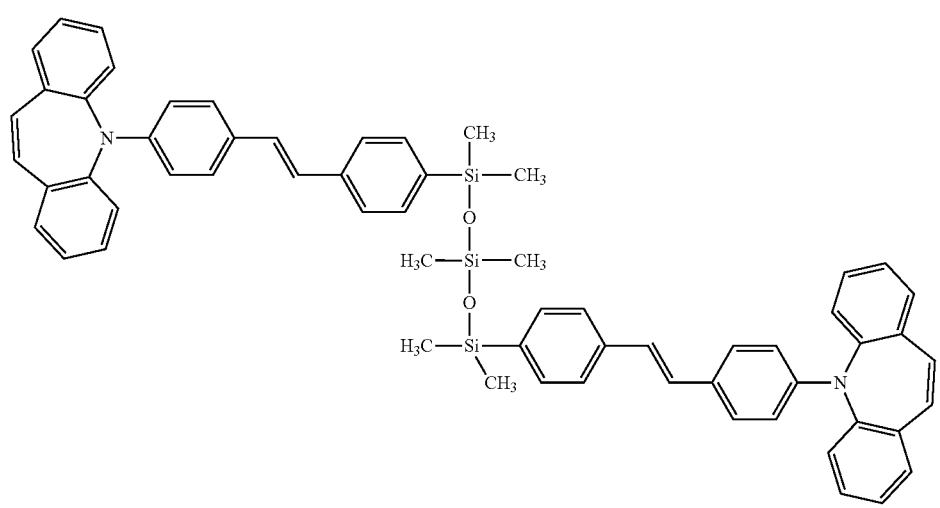

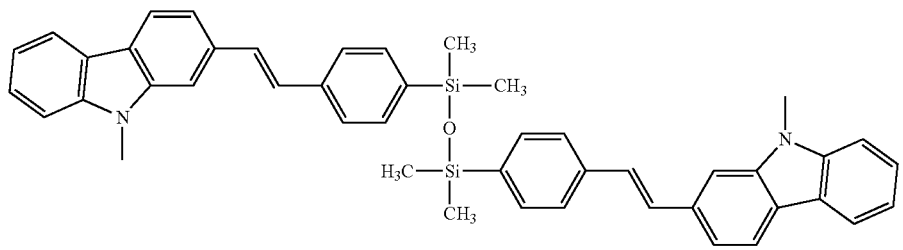

(18)

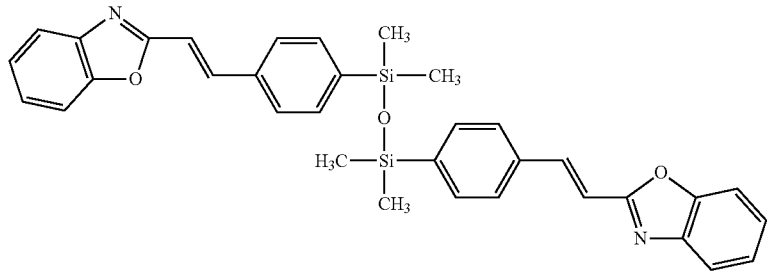

(19)

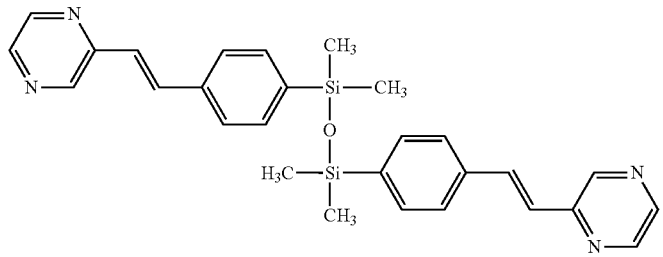

(20)

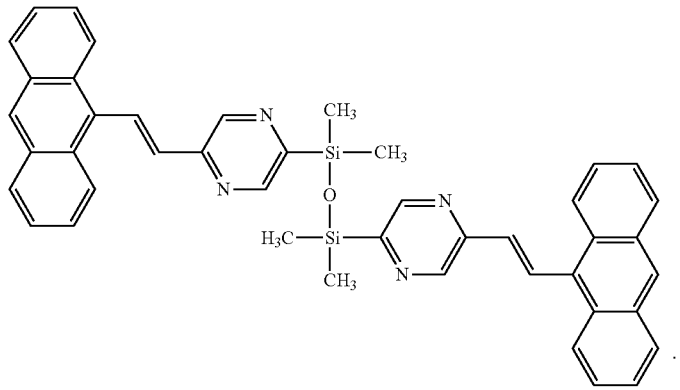

(21)

9. The organosiloxane compound of claim 1, wherein $L_1$, $L_2$, $L_3$, and $L_4$ are each independently a phenylene group, a $(C_1$-$C_{10}$ alkyl)phenylene group, a $(C_1$-$C_{10}$ alkoxy)phenylene group, a halophenylene group, a cyanophenylene group, a dicyanophenylene group, a trifluoromethoxyphenylene group, an o-, m-, or p-tolylene group, an o-, m-, or p-cumenylene group, a mesitylene group, a phenoxyphenylene group, an (α,α-dimethylbenzene)phenylene group, a (N,N'-dimethyl)aminophenylene group, a (N,N'diphenyl)aminophenylene group, a (($C_1$-$C_{10}$ alkyl)cyclohexyl)phenylene group, an (anthracenyl)phenylene group, a biphenylene group, a ($C_1$-$C_{10}$ alkyl)biphenylene group, a ($C_1$-$C_{10}$ alkoxy)biphenylene group, a pentalenyl group, an indenylene group, a naphthylene group, a ($C_1$-$C_{10}$ alkyl)naphthylene group, a ($C_1$-$C_{10}$ alkoxy)naphthylene group, a halonaphthylene group, a cyanonaphthylene group, a biphenylenylene group, a ($C_1$-$C_{10}$ alkyl)biphenylene group, a ($C_1$-$C_{10}$ alkoxy)biphenylene group, an anthracenylene group, an azulenyl group, a hepatarenylene group, an acenaphthylenylene group, a phenalenylene group, a fluorenylene group, an anthraquinolylene group, a methylanthrylene group, a phenanthrenylene group, a triphenylenylene group, a pyrenylene group, a chrysenylene group, an ethyl-chrysenylene group, a picenylene group, a perylenylene group, a chloroperylenylene group, a pentaphenylene group, a pentacenylene group, a tetraphenylene group, a hexaphenylene group, a hexacenylene group, a rubicenylene group, a coronenylene group, a trinaphthylenylene group, a heptaphenylene group, a heptacenylene group, a pyranthrenylene group, an ovalenylene group, a carbazolylene group, a ($C_1$-$C_{10}$ alkyl)carbazolylene group, a thio phenylene group, an indolylene group, a purinylene group, a benzimidazolylene group, a quinolinylene group, a benzothiophenylene group, a parathiazinylene group, a pyrrolylene group, a pyrazolylene group, an imidazolylene group, an imidazolinylene group, an oxazolylene group, a thiazolylene group, a triazolylene group, a tetrazolylene group, an oxadiazolylene group, a pyridinylene group, a pyridazinylene group, a pyrimidinylene group, a pyrazinylene group, a thianthrenylene group, a pyrrolidinylene group, a pyrazolidinylene group, an imidazolidinylene group, a piperidinylene group, a piperazinylene group, or a morpholynylene group;

$L_5$, $L_6$, and $L_7$ are each independently a phenyl group, a ($C_1$-$C_{10}$ alkyl)phenyl group, a ($C_1$-$C_{10}$ alkoxy)phenyl group, a halophenyl group, a cyanophenyl group, a dicyanophenyl group, a trifluoromethoxyphenyl group, an o-, m-, or p-tolyl group, an o-, m-, or p-cumenyl group, a mesityl group, a phenoxyphenyl group, a (N,N'-diphenyl)aminophenyl group, a (($C_1$-$C_{10}$ alkyl)cyclohexyl)phenyl group, an (anthracenyl)phenyl group, a biphenyl group, a ($C_1$-$C_{10}$ alkyl)biphenyl group, a ($C_1$-$C_{10}$ alkoxy)biphenyl group, a pentalenyl group, an indenyl group, a naphthyl group, a ($C_1$-$C_{10}$ alkyl)naphthyl group, a ($C_1$-$C_{10}$ alkoxy)naphthyl group, a halonaphthyl group, a cyanonaphthyl group, a biphenylenyl group, a ($C_1$-$C_{10}$ alkyl)biphenyl group, a ($C_1$-$C_{10}$ alkoxy)biphenyl group, an anthracenyl group, an azulenyl group, a heptarenyl group, an acenaphthylenyl group, a phenalenyl group, a fluorenyl group, an anthraquinolyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, a ($C_{1-10}$ alkyl)carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a pyrrolidinyl group, a pyrazolidinyl group, an imidazolidinyl group, a piperidinyl group, a piperazinyl group, a carbazoryl group, a bezoxazolyl group, a phenothiazinyl group, a 5H-dibenzazepinyl group, a 5H-tribenzazepinyl group, or a morpholynyl group;

$A_1$, $A_2$, $A_3$, $A_4$, $A_5$, and $A_6$ are each independently hydrogen, methyl, ethyl, propyl, butyl, methoxy, ethoxy, a propoxy group, a butoxy group, a phenyl group, a ($C_1$-$C_{10}$ alkyl)phenyl group, a ($C_1$-$C_{10}$ alkoxy)phenyl group, a halophenyl group, a cyanophenyl group, a dicyanophenyl group, a trifluoromethoxyphenyl group, an o-, m-, or p-tolyl group, an o-, m- or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a (($C_1$-$C_{10}$ alkyl)cyclohexyl)phenyl group, an (anthracenyl)phenyl group, a biphenyl group, a ($C_1$-$C_{10}$ alkyl)biphenyl group, a ($C_1$-$C_{10}$ alkoxy)biphenyl group, a pentalenyl group, an indenyl group, a naphthyl group, a ($C_1$-$C_{10}$ alkyl)naphthyl group, a ($C_1$-$C_{10}$ alkoxy)naphthyl group, a halonaphthyl group, a cyanonaphthyl group, a biphenylenyl group, a ($C_1$-$C_{10}$ alkyl)biphenyl group, a ($C_1$-$C_{10}$ alkoxy)biphenyl group, an anthracenyl group, an azulenyl group, a heptarenyl group, an acenaphthylenyl group, a phenalenyl group, a fluorenyl group, an anthraquinolyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, tetraphenylenyl group, hexaphenyl group, hexacenyl group, rubicenyl group, a coronenyl group, a trinaphthylenyl group, a heptaphenyl group, a heptacenyl group, a pyranthrenyl group, an ovalenyl group, a carbazolyl group, a cyclopentyl group, a cyclohexyl group, a ($C_1$-$C_{10}$ alkyl)cyclohexyl group, or a ($C_1$-$C_{10}$ alkoxy)cyclohexyl group; and $B_1$, $B_2$, $B_3$, and $B_4$ are each independently hydrogen, methyl, ethyl, propyl, butyl, a phenyl group, a ($C_1$-$C_{10}$ alkyl)phenyl group, a ($C_1$-$C_{10}$ alkoxy)phenyl group, a halophenyl group, a cyanophenyl group, a dicyanophenyl group, a trifluoromethoxyphenyl group, an o-, m-, or p-tolyl group, an o-, m-, or p-cumenyl group, a mesityl group, a phenoxyphenyl group, an (α,α-dimethylbenzene)phenyl group, a (N,N'-dimethyl)aminophenyl group, a (N,N'-diphenyl)aminophenyl group, a (($C_1$-$C_{10}$ alkyl)cyclohexyl)phenyl group, an (anthracenyl)phenyl group, biphenyl group, a ($C_1$-$C_{10}$ alkyl)biphenyl group, a ($C_1$-$C_{10}$ alkoxy)biphenyl group, a pentalenyl group, an indenyl group, a naphthyl group, a ($C_1$-$C_{10}$ alkyl)naphthyl group, a ($C_1$-$C_{10}$ alkoxy)naphthyl group, a halonaphthyl group, a cyanonaphthyl group, a biphenylenyl group, a ($C_1$-$C_{10}$ alkyl)biphenyl group, a ($C_1$-$C_{10}$ alkoxy)biphenyl group, an anthracenyl group, an azulenyl group, a heptarenyl group, an acenaphthylenyl group, a phenalenyl group, a fluorenyl group, an anthraquinolyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a cyclopentyl group, a cyclohexyl group, a ($C_1$-$C_{10}$ alkyl)cyclohexyl group, or a ($C_1$-$C_{10}$ alkoxy)cyclohexyl group.

10. An organic light-emitting device having the compound of claim 1.

11. The organosiloxane compound of claim 1, wherein $M_1$ and $M_2$ are each independently $L_7$.

* * * * *